(12) United States Patent
Siefert

(10) Patent No.: US 7,543,516 B2
(45) Date of Patent: Jun. 9, 2009

(54) DYNAMIC LEAD SCREW THREAD ENGAGEMENT SYSTEM AND METHOD

(75) Inventor: Robert J. Siefert, Escondido, CA (US)

(73) Assignee: Cardinal Health 303, Inc., San Diego, CA (US)

( * ) Notice: Subject to any disclaimer, the term of this patent is extended or adjusted under 35 U.S.C. 154(b) by 680 days.

(21) Appl. No.: 11/187,115

(22) Filed: Jul. 22, 2005

(65) Prior Publication Data

US 2007/0074596 A1  Apr. 5, 2007

(51) Int. Cl.
F16H 1/18 (2006.01)
(52) U.S. Cl. ............... 74/424.78; 74/424.79; 74/424.94
(58) Field of Classification Search ............... 74/89.37, 74/89.38, 89.39, 89.42, 441, 424.78, 424.79, 74/424.94, 424.95, 424.96
See application file for complete search history.

(56) References Cited

U.S. PATENT DOCUMENTS

| | | | |
|---|---|---|---|
| 3,654,816 A | | 4/1972 | Beery et al. |
| 3,669,440 A | | 6/1972 | Kartasuk et al. |
| 3,858,581 A | * | 1/1975 | Kamen ...................... 604/155 |
| 3,977,269 A | | 8/1976 | Linley, Jr. |
| 3,982,220 A | | 9/1976 | Rozema et al. |
| 4,424,720 A | * | 1/1984 | Bucchianeri ............. 74/424.78 |
| 4,434,677 A | | 3/1984 | Linley, Jr. |
| 4,544,369 A | | 10/1985 | Skakoon et al. |
| 4,767,406 A | * | 8/1988 | Wadham et al. ............. 604/155 |
| 4,833,384 A | | 5/1989 | Munro et al. |
| 4,838,857 A | | 6/1989 | Strowe et al. |
| 4,919,596 A | * | 4/1990 | Slate et al. ..................... 417/18 |
| 5,034,004 A | | 7/1991 | Crankshaw |
| 5,101,679 A | | 4/1992 | Smith et al. |
| 5,106,375 A | | 4/1992 | Conero |
| 5,176,646 A | | 1/1993 | Kuroda |
| 5,236,416 A | * | 8/1993 | McDaniel et al. ............. 604/67 |
| 5,545,140 A | * | 8/1996 | Conero et al. ............... 604/154 |

(Continued)

FOREIGN PATENT DOCUMENTS

EP  0 445 499 A1  9/1991

(Continued)

OTHER PUBLICATIONS

International Search Report, PCT/US2006/027780, International Filing Date: Jul. 19, 2006, Cardinal Health 303, Inc.

*Primary Examiner*—David M Fenstermacher
(74) *Attorney, Agent, or Firm*—McDermott Will & Emery

(57) ABSTRACT

A system and method for automatically aligning the threads of a lead screw with the threads of a screw drive mechanism, the screw drive mechanism operating to translate the rotational motion of the lead screw into linear motion to expel the contents of a mounted syringe. The system comprises a driver position sensor for determining the position of the screw drive mechanism along the lead screw and a processor for receiving position signals from the driver position sensor, for determining a requisite rotation of the lead screw to ensure alignment of the two sets of threads, and for effectuating the requisite rotation of the lead screw to achieve that alignment. An automatic calibration routine is included that checks for variances in calibration of the system and if found, updates a conversion factor to restore accuracy. Various sensors are used to monitor the operation of components.

12 Claims, 15 Drawing Sheets

U.S. PATENT DOCUMENTS

| | | | |
|---|---|---|---|
| 5,567,122 A | 10/1996 | Schulte | |
| 5,713,242 A * | 2/1998 | Kanner et al. | 74/424.78 |
| 5,879,360 A * | 3/1999 | Crankshaw | 606/154 |
| 5,925,018 A | 7/1999 | Ungerstedt | |
| 5,954,697 A | 9/1999 | Srisathapat et al. | |
| 6,248,093 B1 | 6/2001 | Moberg | |
| 6,575,936 B1 | 6/2003 | Kojima et al. | |
| 2002/0020234 A1 | 2/2002 | Smith et al. | |
| 2004/0176725 A1 | 9/2004 | Stutz, Jr. et al. | |

FOREIGN PATENT DOCUMENTS

| | | |
|---|---|---|
| EP | 0 514 816 A1 | 11/1992 |
| EP | 0514907 A1 | 11/1992 |
| EP | 1110569 A2 | 6/2001 |
| EP | 1066846 A1 | 10/2001 |

* cited by examiner

DYNAMIC LEAD SCREW THREAD ENGAGEMENT SYSTEM AND METHOD

FIELD OF THE INVENTION

The invention is related generally to screw drive mechanisms, and more particularly, to an engagement system and method for engaging a driver with a lead screw.

BACKGROUND OF THE INVENTION

The infusion of fluids such as parenteral fluids into the human body is accomplished in many cases by means of a syringe pump having a lead screw on which a screw drive mechanism is mounted. Rotation of the lead screw is translated into linear motion by the screw drive mechanism. The linear motion is transmitted to a syringe plunger by a plunger driver that is typically rigidly connected to the screw drive mechanism. To facilitate replacement of an empty syringe, split nuts or half nuts are used as part of the screw drive mechanism in some syringe pumps for easy and rapid repositioning of the screw drive mechanism and plunger driver on the lead screw to engage the syringe plunger of a full syringe with the plunger driver. An activating lever or other mechanical interface for the operator is provided at the plunger driver to separate the split nut threads from the lead screw threads and to separate the plunger driver from the present syringe plunger. The plunger driver is then manually moved away from the empty syringe so that it can be removed. In the case where a new syringe is to be loaded into the syringe pump, the operator continues to manipulate the activating lever or other mechanical interface to disengage the split nuts from the lead screw, move the plunger driver and split nuts along the lead screw to an appropriate position, and inserts the new syringe into the pump. The operator then moves the plunger driver into contact with the plunger flange of the new syringe, releases the activating lever when the plunger driver is pressed against the syringe plunger, and thereby allows the split nuts to drop onto the lead screw. Ideally, the crests of the split nut threads drop as far as possibly into the troughs of the lead screw threads so that the threads of both devices are fully engaged. Unfortunately, the threads do not always fully engage.

As shown in FIG. 1, in some cases the crests of the split nut threads 10 undesirably align with and contact the crests of the lead screw threads 12 rather than the threads engaging each other. Because either set of the threads may be relatively flat at their crests, they do not engage each other until the lead screw has turned a sufficient amount and a bias device of the screw drive mechanism has forced the split nut threads to drop into and engage the lead screw threads. Under low infusion rates, such sufficient lead screw rotation may take a substantial amount of time during which the patient receives no infusion fluid.

In another case as presented in FIG. 2, the non-driving surfaces of the split nut threads 10 may undesirably contact the non-driving surfaces of the lead screw threads 12 when the activating lever is released. The arrow indicates the direction of forward movement of the split nuts and plunger driver. Due to the thread clearance 14 between the two sets of threads, some amount of time may pass before the driving surfaces of the lead screw threads 12 fully engage the driving surfaces of the split nut threads 10 and actually begin to move the syringe plunger along with the split nuts. This amount of time also would be a period during which the patient receives no infusion fluid.

In yet another case as presented in FIG. 3, the driving surfaces of the split nut threads 10 may only partially engage the driving surfaces of the lead screw threads 12. Partial engagement occurs when the crests of the split nut threads 10 fail to drop completely into the troughs of the lead screw threads 12. When this occurs, a large amount of back pressure exerted by the full syringe and a force vector developed by the lead screw threads 12 tend to force the split nut threads 10 up and out of the lead screw threads 12. If the biasing force on the split nuts is insufficient to overcome these factors, the split nut threads 10 may be forced out of contact with the driving surfaces of the lead screw threads 12 and into the position shown in FIG. 1. This case would likewise result in a time period during which the patient would receive no infusion fluid and this time period may exceed that associated with FIG. 1.

Under low infusion rates, it could be an hour or more before non-engagement or partial engagement conditions illustrated in FIGS. 1-3 and the resulting failure to deliver infusion fluid are discovered and corrected or automatically overcome by the slow rotation of the lead screw. This problem is only partially overcome in a prior system that automatically rotates the lead screw in a forward direction to remove any thread clearance or in a combination of reverse and forward directions to fully seat the split nut threads then remove any thread clearance. An engagement sensor is employed to give a positive engagement signal when the split nut threads were seated within in the lead screw threads at or below a point corresponding to a percentage of root thread depth deemed to represent sufficient engagement. If the engagement signal was positive, the lead screw is automatically rotated a fixed amount in the forward direction to remove any thread clearance. This occurs even when the split nut threads 10 happen to be already fully seated. Thus, the automatic rotation could move the syringe plunger along with split nuts and cause excessive fluid infusion. If the engagement signal was negative, the lead screw is rotated a fixed amount in the reverse direction and another reading of the engagement sensor is taken. If the engagement signal remained negative, the lead screw would be rotated again by some fixed amount in the reverse direction and a reading of the engagement sensor is taken again. The reverse rotations would be repeated a fixed number of times, after which the lead screw would be rotated by some fixed amount in the forward direction followed by another reading of the engagement sensor. An alarm would be set off after a fixed number of unsuccessful attempts at thread engagement. If after any attempt the split nut threads were deemed sufficiently seated, the lead screw would be automatically rotated a fixed amount in the forward direction to remove any possible thread clearance. Thus, the prior system always rotates the lead screw by a fixed amount independent of the linear position of the crests of the split nut threads relative to the crests of the lead screw threads.

In addition, the automatic rotation in the prior system is initiated after a signal from a plunger sensor indicates that a syringe plunger is present and after a signal from the engagement sensor indicates that the split nut threads 10 are not sufficiently seated. Undesirably, the rotation occurs prematurely in some instances when a negative indication from the engagement sensor arises from the operator having failed to release the activating lever, not because the crests of the split nut threads 10 are resting on the crests of the lead screw threads 12.

Thus, when the automatic rotation routine has completed and the operator subsequently releases the activating lever, the two sets of threads may again be in one of the positions shown in FIGS. 1-3 and result in delayed fluid infusion. The resulting delayed and excessive fluid infusion associated with syringe replacement as may occur in prior systems is undesirable under low infusion rates where more precise and accurate control of fluid infusion is required.

Hence, those skilled in the art have recognized a need for an improved lead screw engagement system that reduces the possibility of delayed and excessive fluid infusion associated with syringe mounting in the pump. The present invention fulfills this need and others.

SUMMARY OF THE INVENTION

The present invention is directed to a system and method that automatically aligns the threads of a screw drive mechanism with the threads of a lead screw of a syringe infusion pump at the time the two are engaged to reduce the possibility of an occurrence of delayed or excessive fluid infusion and, thus, allows for more precise and accurate control over fluid infusion.

In one aspect of the present invention, the system for aligning threads of a lead screw with threads of a screw drive mechanism for full thread engagement comprises a motor coupled to the lead screw, a plunger driver coupled to the screw drive mechanism, a position sensor that provides a position signal representative of an axial position of the screw drive mechanism along the lead screw, a release device that disengages the threads of the screw drive mechanism from engagement with the threads of the lead screw, and a processor that receives position signals from the position sensor and controls the motor to rotate the lead screw to a predetermined rotational position based on the position signals. The release device allows an operator to move the screw drive mechanism to a selected position along the lead screw at which the threads of the screw drive mechanism may be re-engaged with the threads of the lead screw.

In another aspect, the processor receives the position signal from the position sensor indicative of the position at which the operator is re-engaging the threads of the screw drive mechanism with the threads of the lead screw; and the processor controls the motor to rotate the lead screw to a position at which the threads of the lead screw are aligned with the threads of the screw drive mechanism at the position selected by the operator.

In yet another aspect, the threads of the lead screw have a pitch, the threads of the screw drive mechanism have a pitch, and the processor controls the motor to rotate the lead screw to a position at which the two sets threads are aligned as the threads are being re-engaged. The position is based on receipt of the position signal and based on the thread pitch of at least one of the lead screw and the screw drive mechanism.

In one aspect, the system for aligning threads includes a memory in which is stored a reference position along the lead screw at which the two sets of threads have been aligned and fully engaged with each other. In this aspect, the processor compares the position signal to the reference position, and controls the motor to rotate the lead screw to a position at which the two sets of threads aligned as the lead screw and screw drive mechanism threads are being re-engaged.

In another aspect, the system for aligning threads includes a syringe plunger sensor that provides a plunger sensor signal upon detecting the engagement of a syringe plunger with the plunger driver. In this aspect, upon the processor receiving the plunger sensor signal, the processor compares the position signal to the reference position, and controls the motor to rotate the lead screw to a position at which the two sets of threads are aligned as the threads are being re-engaged.

In yet another aspect, the system for aligning threads includes a thread engagement sensor that provides a thread engagement signal upon detecting that the threads of the screw drive mechanism are fully engaged with the threads of the lead screw. In this aspect, upon receiving the thread engagement signal, the processor stores the position of the screw drive mechanism along the lead screw as a reference position. Also, the processor compares the position signal to the reference position, and controls the motor to rotate the lead screw to a rotational position at which two sets of threads are aligned as the threads are being re-engaged.

In one aspect, the position sensor provides an electrical position signal representative of the axial position of the screw drive mechanism in relation to the lead screw, and processes the position signal with a conversion factor to determine the axial location of the screw drive mechanism in relation to the lead screw.

In a further aspect, the system for aligning threads includes a thread engagement sensor that provides a thread engagement signal upon detecting that the two sets of threads are threads of the screw drive mechanism are fully engaged with the threads of the lead screw. In this aspect, upon receiving the thread engagement signal, the processor stores the position of the screw drive mechanism along the lead screw as a reference position. In addition, the processor compares the position signal to the reference position, and controls the motor to rotate the lead screw to a rotational position at which the two sets of threads are aligned as the threads are being re-engaged.

In a still further aspect, the processor monitors the thread engagement signal upon re-engagement of the threads of the screw drive mechanism with the threads of the led screw and if the thread engagement signal is not received, the processor alters the conversion factor.

Other features and advantages of the present invention will become apparent from the following detailed description, taken in conjunction with the accompanying drawings, which illustrate, by way of example, the principles of the invention.

DETAILED DESCRIPTION OF THE INVENTION

Figure 1:
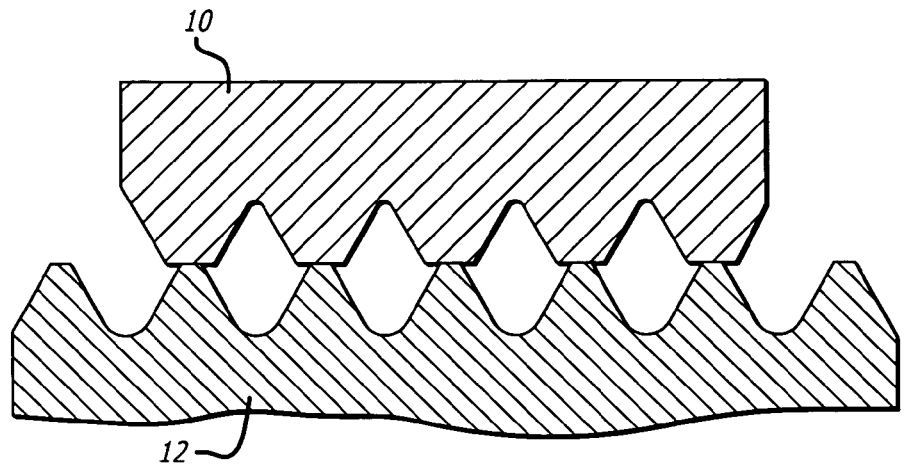
FIG. 1 presents a cross-sectional view of the threads of a lead screw and threads of a split not showing the crests of the threads on the split nut resting on the crests of the threads on the lead screw resulting in effective disengagement of the two sets of threads.
Figure 2:
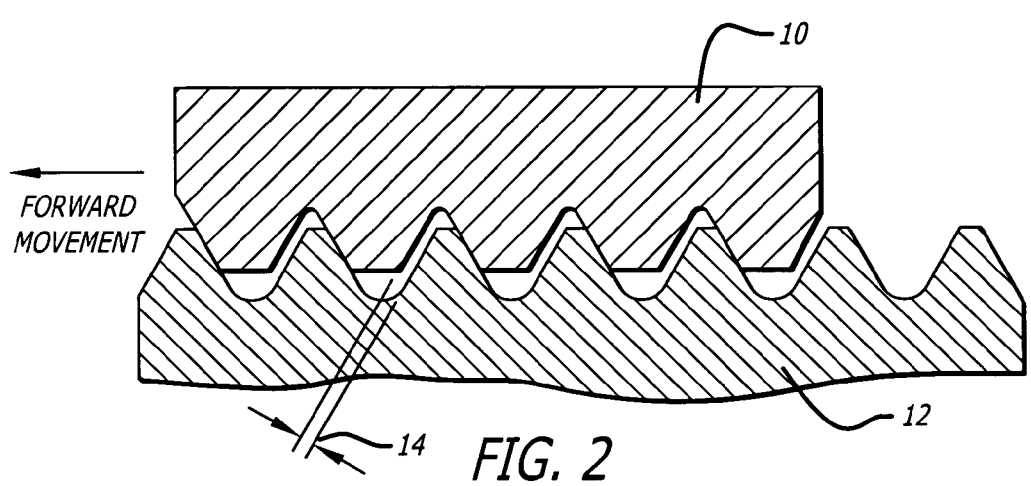
FIG. 2 presents a cross-sectional view of the non-driving surfaces of the threads of a split nut contacting the non-driving surfaces of the threads of a lead screw and shows the resulting thread clearance.
Figure 3:
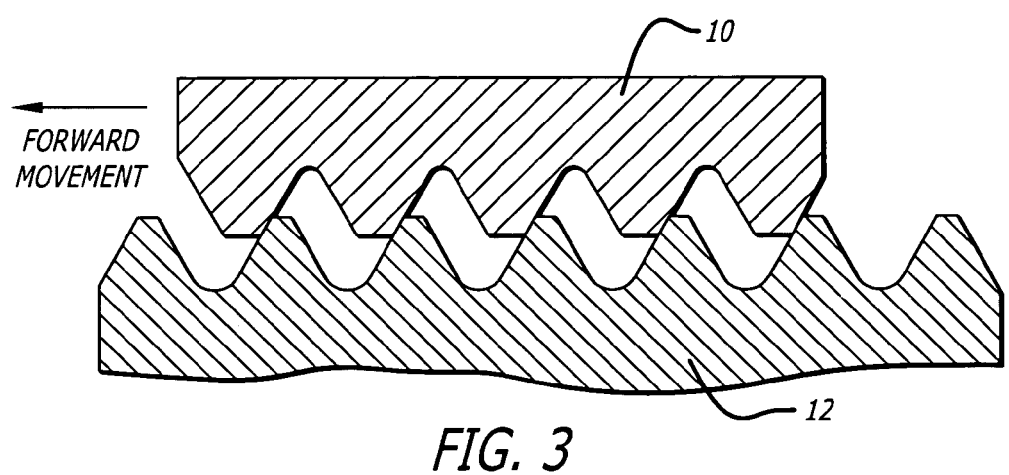
FIG. 3 presents a cross-sectional view of a partial engagement of the threads of the split nut with the threads of the lead screw.
Figure 4:
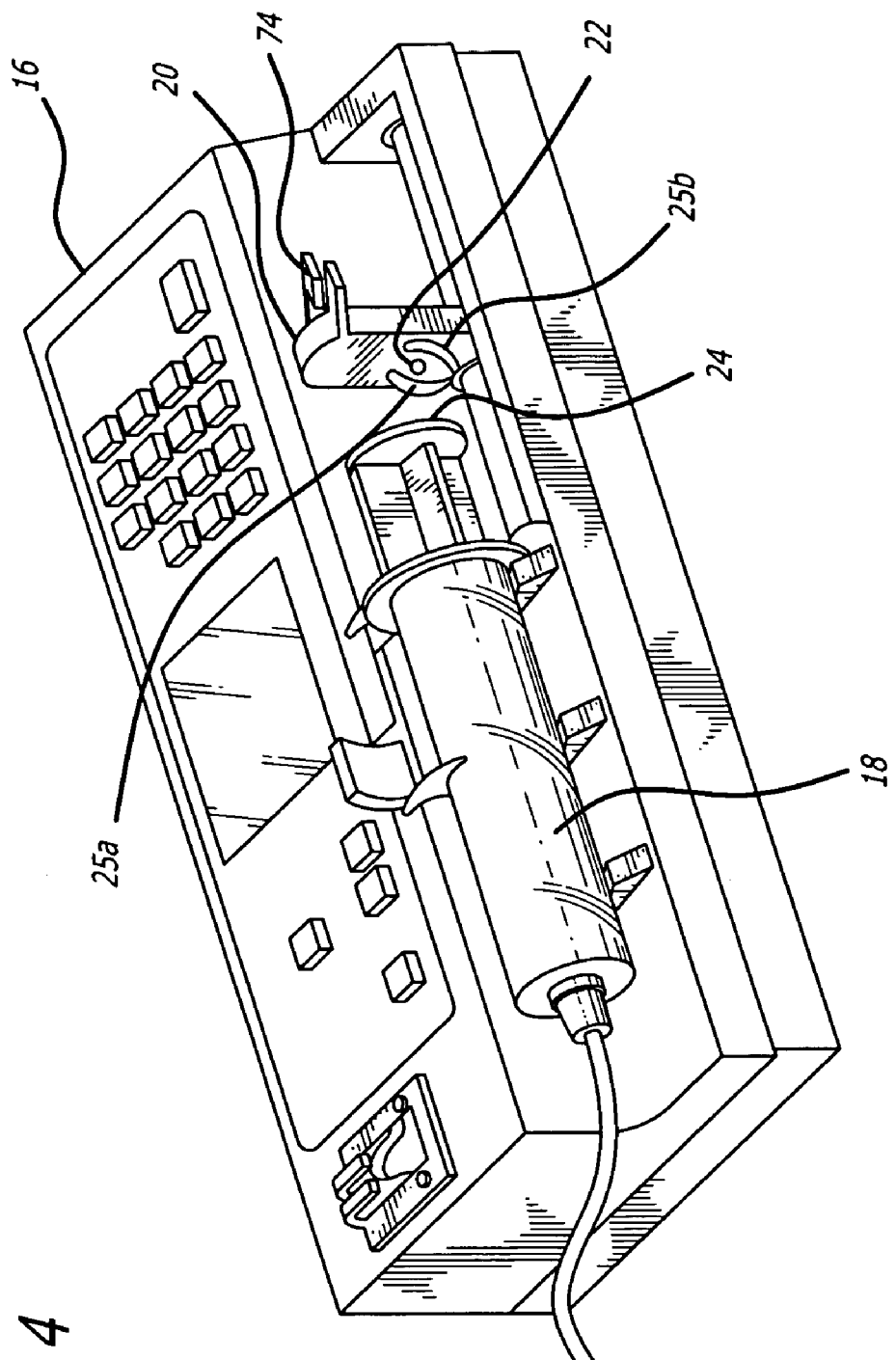
FIG. 4 presents a perspective view of a syringe pump showing a syringe mounted in the pump with the plunger driver retracted away from the syringe plunger prior to its engagement with the plunger flange to begin infusion of the syringe barrel contents.

Referring now to the exemplary drawings wherein like reference numerals designate like or corresponding elements among the several views there is shown in FIG. 4 a syringe pump 16 having a syringe 18 mounted in the pump. A plunger driver 20 not yet engaged with the syringe plunger flange 24 includes a plunger sensor button 22 which is used to detect the presence of a syringe plunger 24 pressed against the plunger driver. During fluid infusion, the plunger driver presses against the syringe plunger. In FIG. 4, the plunger driver is retracted rearward away from the syringe plunger so that the plunger sensor button may be seen. The syringe plunger driver also includes two rotating arms 25a and 25b in this embodiment that will capture the syringe plunger flange against the driver to prevent siphoning from the syringe.

Figure 5:
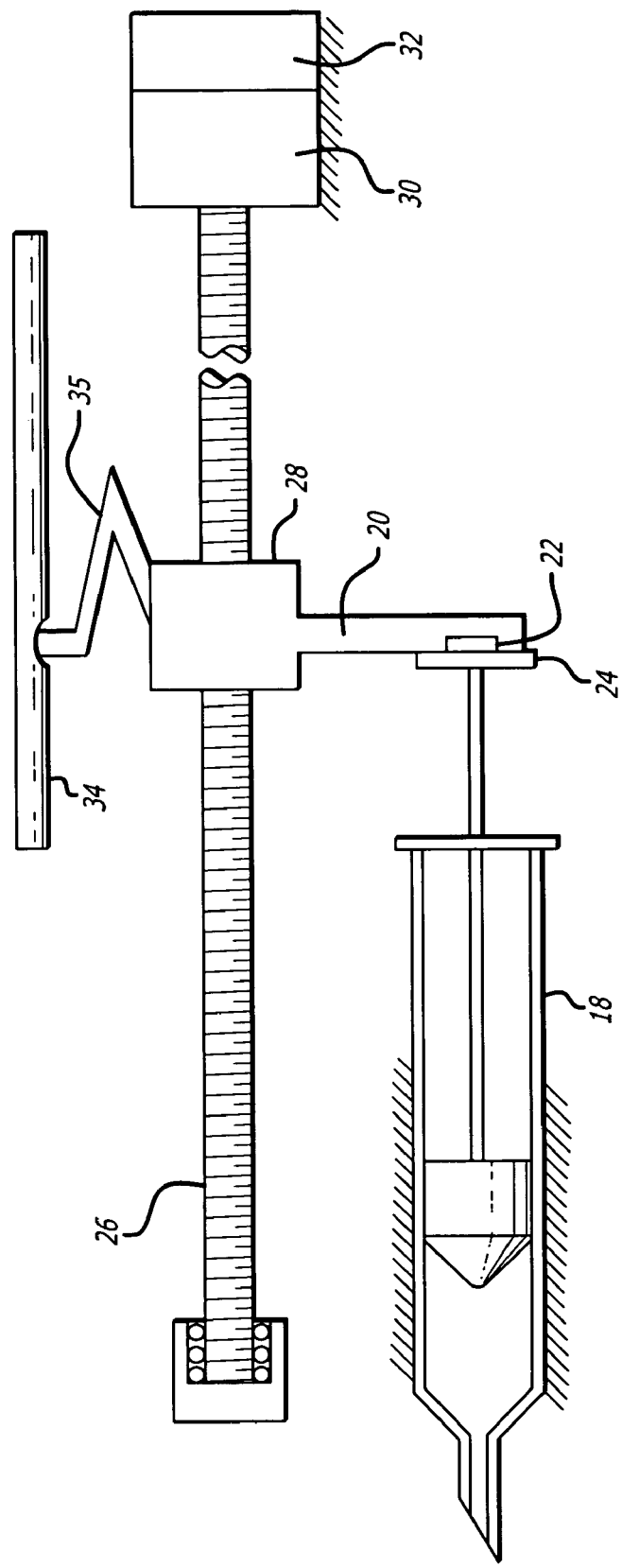
FIG. 5 presents a block diagram of a dynamic thread engagement system and shows a screw drive mechanism including a lead screw, motor drive, motor controller, bearing, and showing the plunger driver coupled to a driver position sensor.

Referring now to FIG. 5, a lead screw 26 is in thread engagement with a moveable screw drive mechanism 28 that is coupled to the plunger driver 20. The screw drive mechanism has a thread engagement mechanism to selectively engage or disengage it from the lead screw. The engagement mechanism is of a half-nut or split-nut design, described in more detail below. Rotational motion of the lead screw is translated to linear motion by the screw drive mechanism. The rate of rotation of the motor 30, controlled by a suitable motor control 32, determines the rate of linear movement of the plunger driver. The position of the screw drive mechanism is sensed by means of a suitable high-resolution position sensor, referred to herein as a driver position sensor 34, which provides position signals representative of the position of the screw drive mechanism and plunger driver along the lead screw. The driver position sensor may comprise a stationary potentiometer that extends along the lead screw through the range of travel of the screw drive mechanism. However, the driver position sensor may take many forms. As one example, the sensor may comprise a potentiometer having narrow, flat strips of material that are parallel to each other. One layer is shorting or non-resistive in nature and another layer, to which a power source $V_b$ is applied, is resistive in nature. A finger-like wiper 35 fixedly attached to the screw drive mechanism presses upon the shorting layer with enough force to cause the shorting layer to contact the resistive layer. Thus, as the screw drive mechanism is moved, a voltage $V_O$ (between $V_b$ and the ground potential) across the resistive layer is developed at the contact point. Preferably, the potentiometer of the driver position sensor has an accuracy of at least +/−0.013 cm (+/−0.005 inches) such as provided by conductive plastic motion transducer element KITLMF5D103 manufactured by Vishay Sfernice (Malvern, Pa.). It will be appreciated that other suitable types of sensors having the same or better accuracy may be used and depending on the application of the pump, a lesser accuracy may prove to be suitable.

Figure 6:
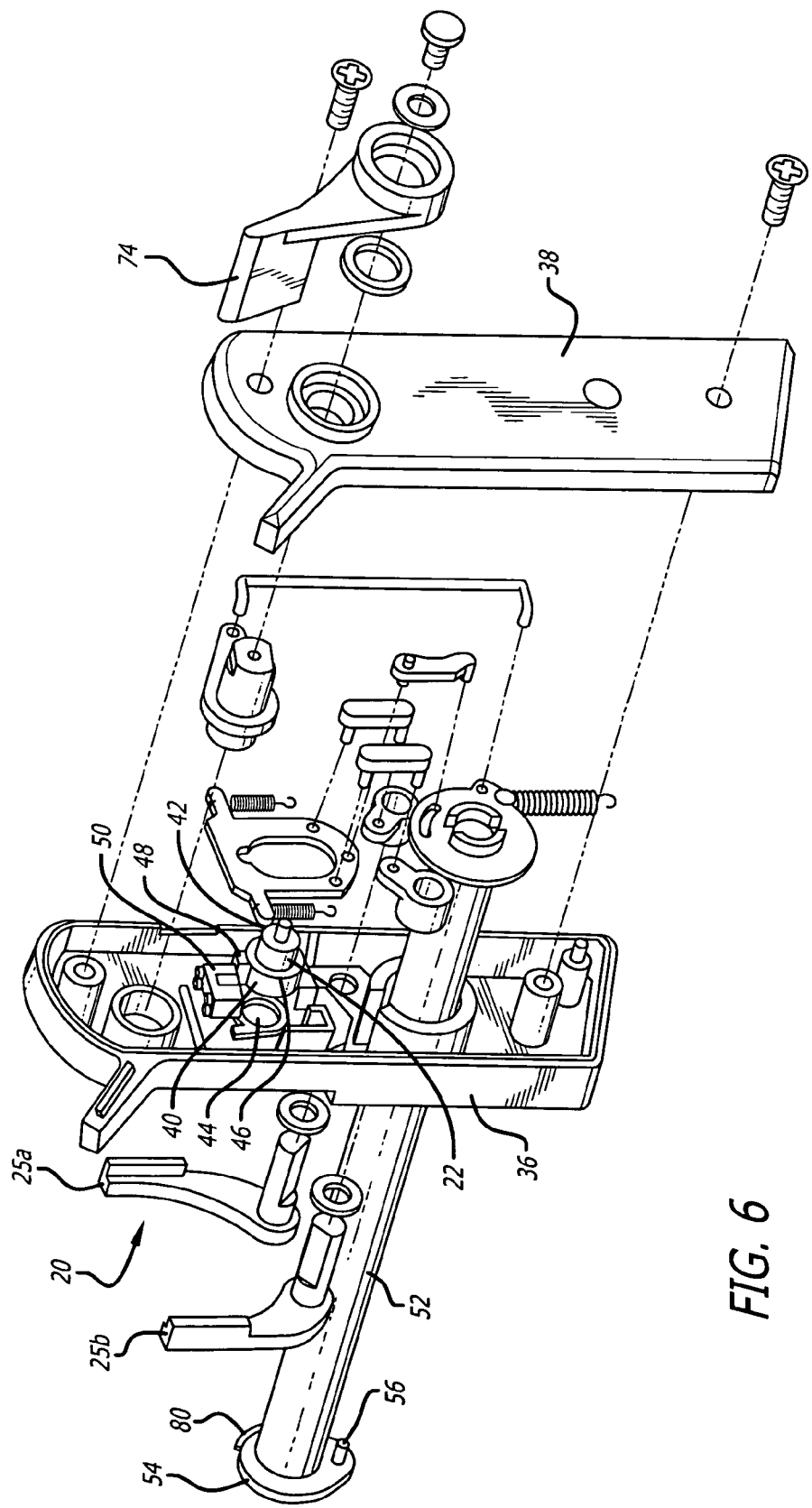
FIG. 6 presents is an exploded detail view of the plunger driver of FIG. 4 and shows a plunger sensor and an activating lever, the lever being coupled to a split nut tube.

Referring now to FIG. 6, an exploded view of an example of a plunger driver 20 is shown. The front housing 36 has been separated from the rear housing 38 to view the plunger sensor button 22 in more detail. The plunger sensor button has been withdrawn from its normal position in the front housing. The plunger sensor button has a beveled front surface 40 to allow additional flexibility in installing the syringe 18. The plunger sensor button has a spring 42 to provide a bias of the plunger sensor button outward toward the syringe plunger 24 (shown in FIG. 4). In this embodiment, the spring rests against the rear housing to push the plunger sensor button to extend out of the front housing through an aperture 44. The plunger sensor button includes an annular stop flange 46 to retain the plunger sensor button in the front housing. The plunger sensor button will extend through the aperture formed in the front housing to press against the syringe plunger 24 of an installed syringe.

The plunger sensor button 22 also includes a flag 48 for indicating the position of the plunger sensor button and the presence of a syringe plunger 24. A first optical beam sensor, referred to herein as a plunger sensor 50, is mounted above the plunger sensor button but in line with the flag to determine the position of the flag. The plunger sensor provides a plunger signal indicating whether the plunger driver 20 is pressed against a syringe plunger. The trip point for the plunger sensor depends on the position of the flag relative to the sensor. Preferably, the trip point is set such that the plunger signal indicates that the plunger driver is pressed against the syringe plunger when the plunger sensor button has been pushed back through the aperture 44 so as to be almost flush with the front housing 36 of the plunger driver. Further details may be found in U.S. Pat. No. 5,106,375 to Conero, incorporated herein by reference. As shown, the plunger driver is connected to a split nut tube 52.

Figure 7:
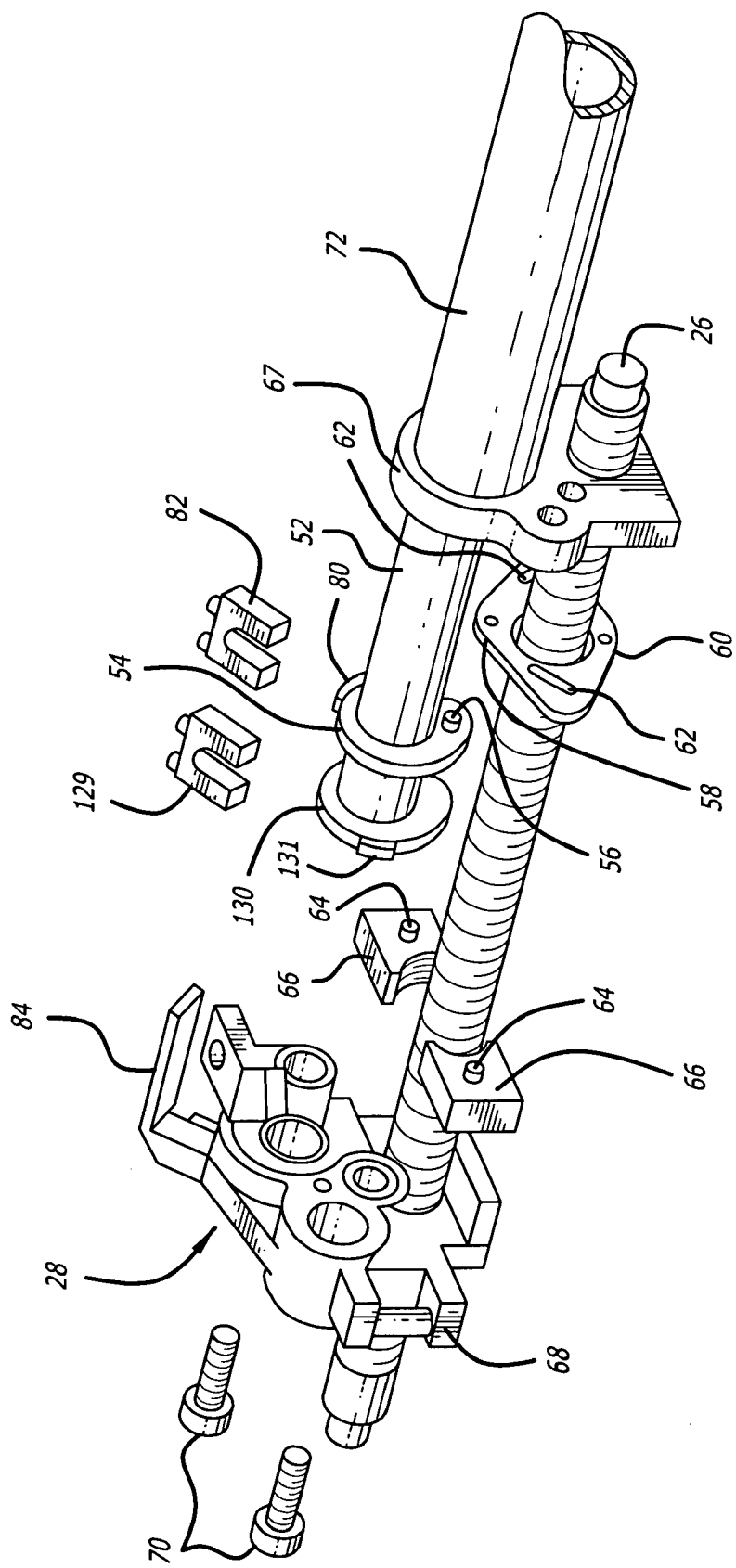
FIG. 7 presents an exploded detail view of the split nuts, a lever sensor, and a thread engagement sensor and shows them being coupled to the split nut tube, showing the lever sensor disposed to sense actuating of the activating lever, and showing the engagement sensor disposed to sense the position of the split nuts in relation to the lead screw threads.

Referring now to FIG. 7, an exploded view of a screw drive mechanism 28 is shown. The screw drive mechanism is mounted on lead screw 26 and includes the split nut tube 52 having a first flange 54 on which is mounted a pin 56 for engaging an upper slot 58 on a cam plate 60. The cam plate also includes two elongate slots 62, each for engaging a pin 64 on each of two split nuts 66. The split nuts and the cam plate are sandwiched between a support plate 67 and a split nut housing 68 and held in position by screws 70. Accordingly, rotation of the split nut tube rotates the cam plate, which in turn separates the split nuts from the threads of the lead screw.

The drive tube 72 rigidly couples the screw drive mechanism 28 to the plunger driver 20. Thus, linear motion of the screw drive mechanism arising from lead screw rotation is transmitted to the plunger driver and movement of the plunger driver by the operator will move with the screw drive mechanism. The activating lever 74 (shown in FIGS. 4 and 6) on the plunger driver 20 is rigidly coupled to the split nut tube 52 such that pressing the activating lever results in rotation of the split nut tube and separation of the split nuts 66 from the threads of the lead screw 26. Releasing the activating lever 74 causes the split nuts 66 to contact the threads of the lead screw.

Referring to both FIGS. 6 and 7, a flag 80 is rigidly mounted on the first flange 54 of the split nut tube 52. Pressing the activating lever 74 to separate the split nuts 66 from the lead screw 26 rotates the flag. A second optical beam sensor, referred to herein as a lever sensor 82, is mounted on a platform 84 forming part of the split nut housing 68 and detects the position of the flag. The lever sensor provides a lever signal indicating the rotational position of the activating lever, which is related to the depth at which the split nut threads are seated within the lead screw threads. The relationship between the rotation of the activating lever and movement of the split nuts depends on the shape of the elongate slots 62 engaging the split nut pins 64.

Figure 8:
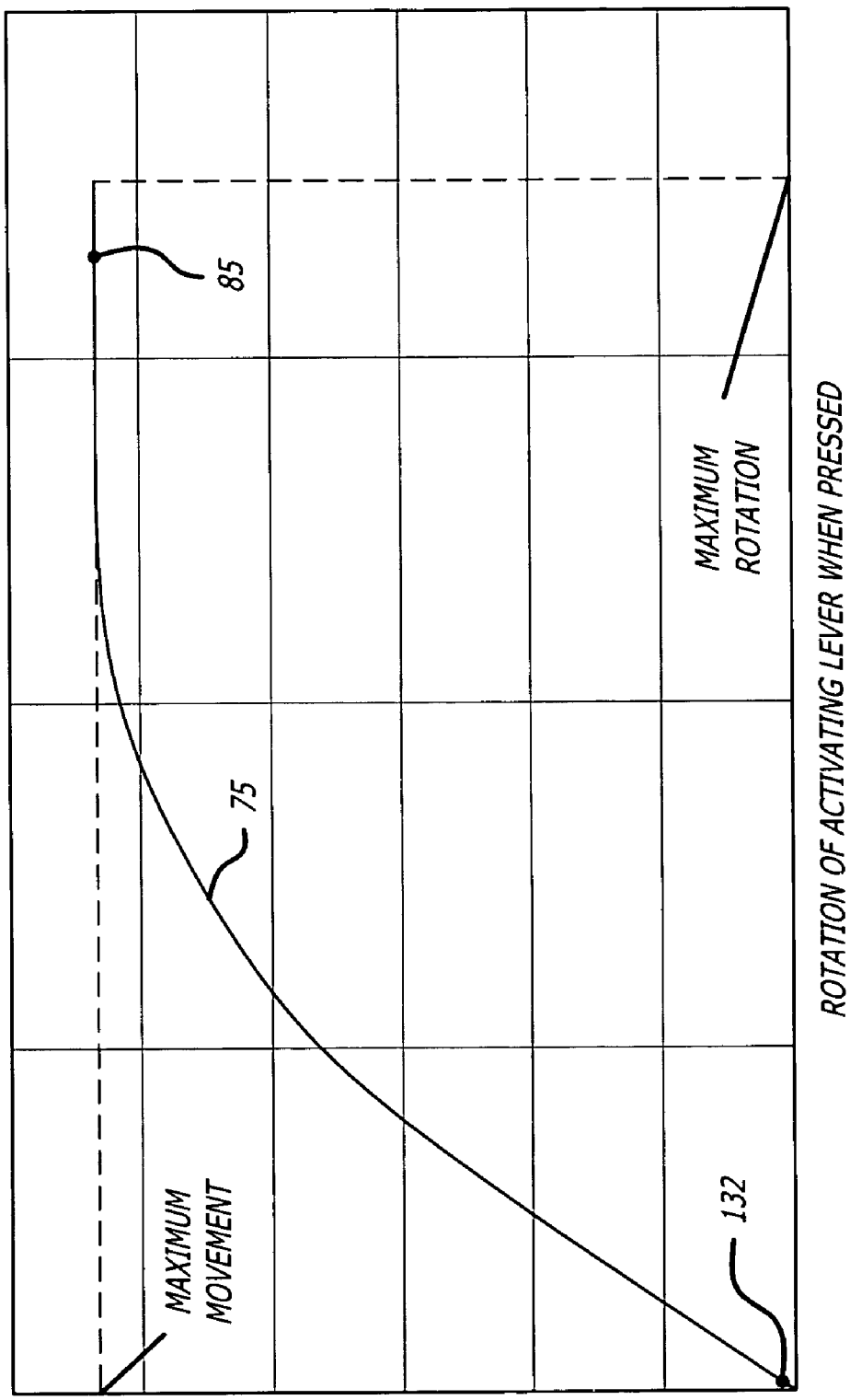
FIG. 8 presents a graph of a curvilinear relationship between rotation of the activating lever in FIG. 6 and radial movement of the split nuts in FIG. 7, and shows a trip point for the lever sensor on the upper, flat portion of the curve.

Referring now to FIG. 8, the relationship between the rotation of the activating lever 74 and movement of the split nuts 66 away from the lead screw 26 is illustrated as a non-linear curve 75. The trip point for the lever sensor 82 depends on the position of the flag 80 relative to the sensor 82 when the activating lever has been released and is at rest. Preferably, the trip point for the lever signal is set at a point 85 on the curve in FIG. 8 corresponding to near maximum lever rotation when pressed and maximum separation of the split nuts from the lead screw. In this embodiment, when the operator presses the activating lever completely, the flag will interrupt the beam of the lever sensor causing the lever signal to indicate that the split nuts threads are completely separated from the lead screw threads. When the operator begins to release the activating lever, the slight movement of the flag, before the split nut threads drop within the lead screw threads, will cause the lever signal to indicate that the split nuts threads have begun to move radially toward the lead screw threads.

Figure 9:
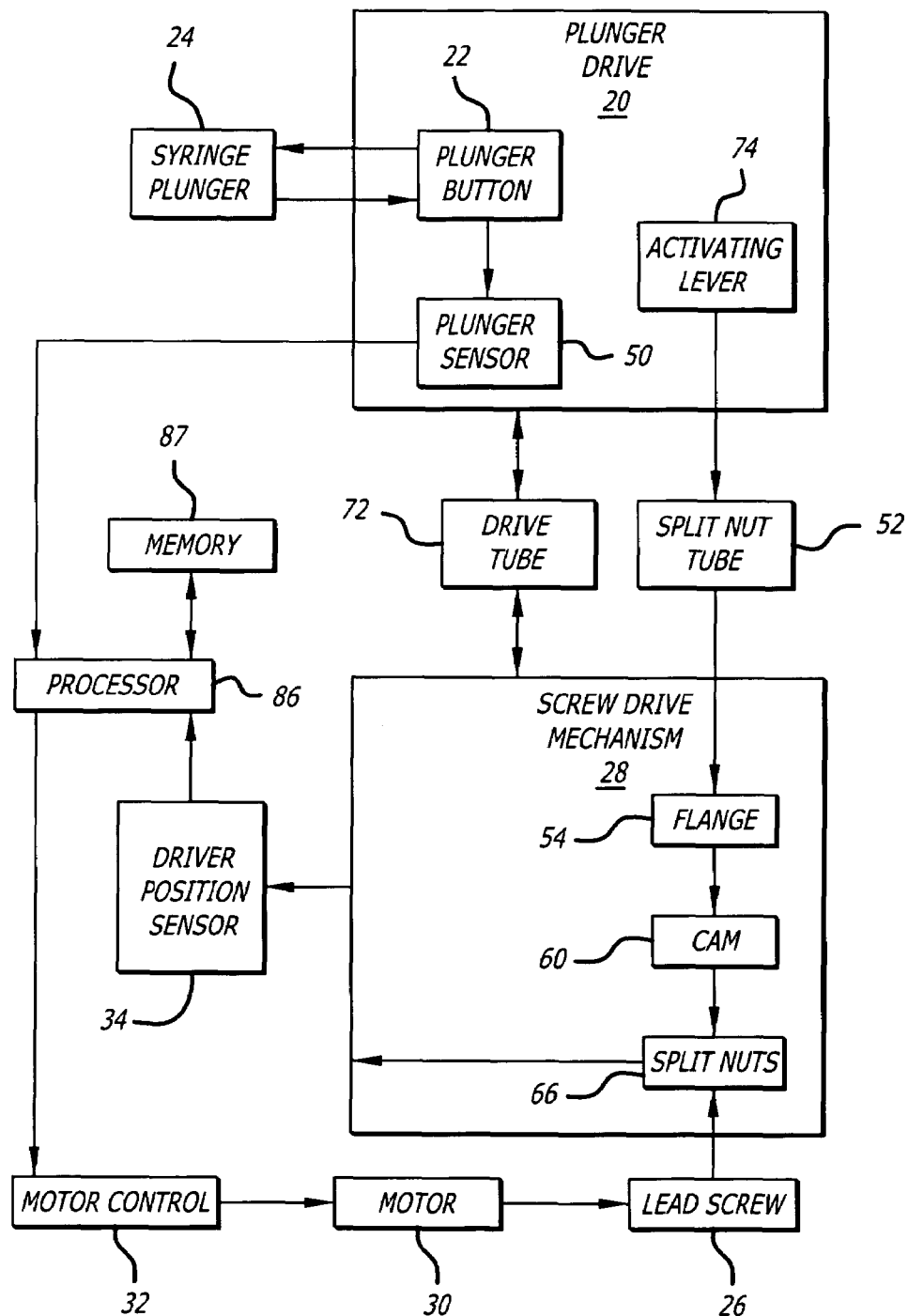
FIG. 9 presents is a block diagram of a dynamic engagement system having the signal from the plunger sensor and from the driver position sensor coupled to a processor to control alignment of the split nut threads with the lead screw threads.

Referring now to FIG. 9, an embodiment is shown having both signals from the plunger sensor 50 and from the driver position sensor 34 coupled to a processor 86. The processor analyzes these signals and based on various factors as discussed below, provides a signal to the motor control 32 to control rotation of the lead screw. Depending on the information content of the signal from the processor, the motor control may control the motor 30 to rotate the lead screw.

Figure 10:
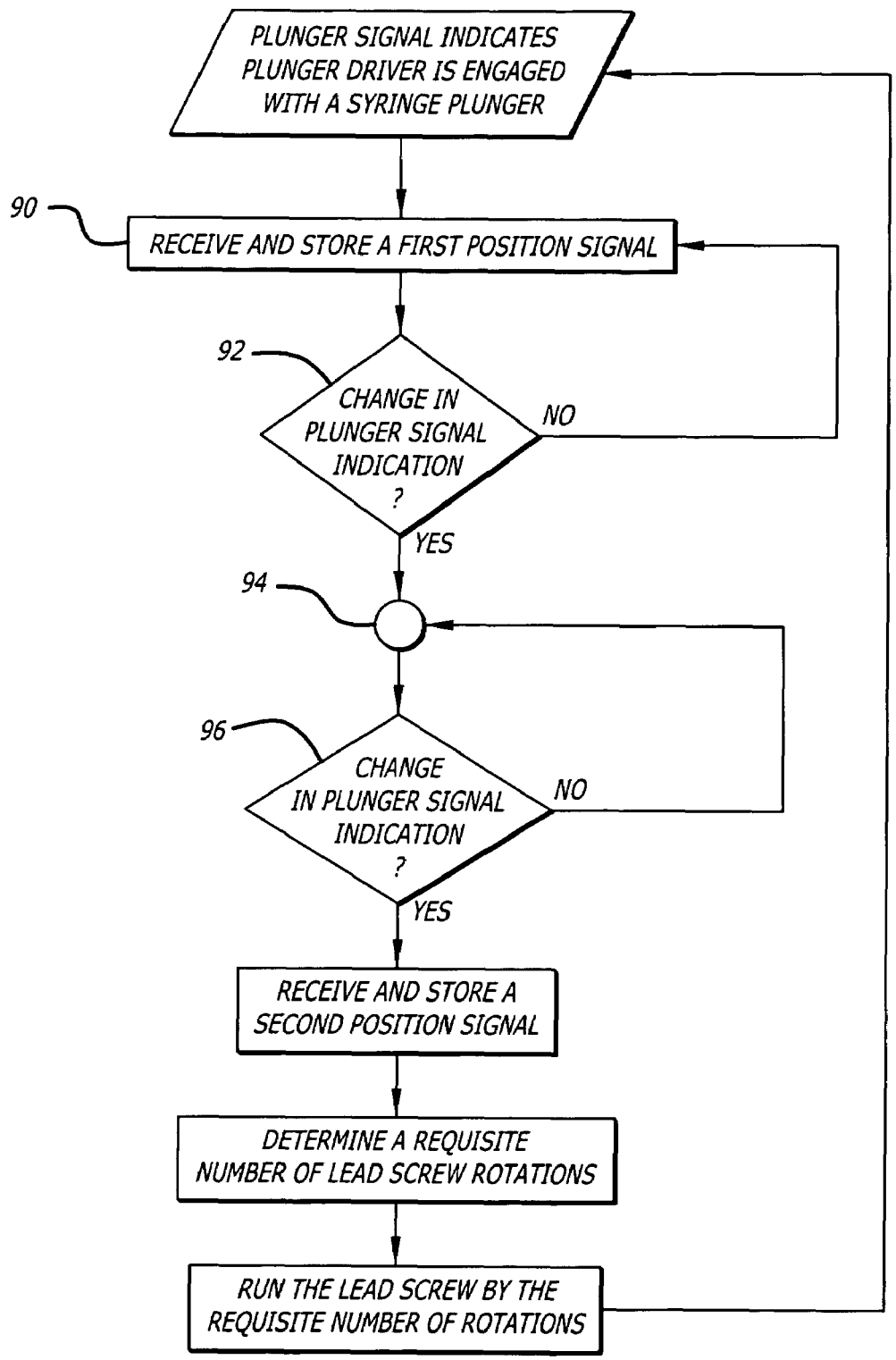
FIG. 10 presents a flow diagram of a dynamic engagement method using the signal from the plunger sensor to control thread alignment.

Referring now to FIG. 10, there is shown an operational flow diagram illustrating a method in which the plunger signal (indicating the existence or nonexistence of a plunger engaged by the plunger driver) is used by the processor to detect syringe replacement and to infer disengagement of the split nut threads from the lead screw threads. Between blocks 90 and 92 of the flow diagram, the operator presses the activating lever 74 in order to remove a first syringe requiring replacement from the syringe pump 16. In so doing, the split nuts 66 disengage from the lead screw 26 to allow the operator to slide the plunger driver 20 rearward away from the syringe so that the syringe may be removed. Accordingly, at block 92, the plunger signal from the plunger sensor 50 to the processor 86 indicates that the plunger driver is disengaged from the plunger of the syringe to be removed. The processor infers from this change in the plunger signal that the threads of the split nuts have just disengaged from the threads of the lead screw. Before the change in the plunger signal and while the split nut threads were fully engaged with the lead screw threads, the processor 86 received and stored a first position signal from the driver position sensor 34. At block 94, subsequent to installing a second syringe in place of the first syringe, the operator slides the plunger driver forward so that it presses against the syringe plunger of the second syringe. Accordingly at block 96, the plunger signal now indicates that the plunger driver is engaged with the syringe plunger of the second syringe that has replaced the first syringe. Upon or after this indication, the processor receives and stores a second position signal from the driver position sensor. Using the first position signal and the second position signal, the processor determines a necessary amount of lead screw rotation to cause the split nut threads fully engage the lead screw threads when the split nuts are released from their retracted position and move toward engagement of the lead screw threads. If the number is non-zero, the processor 86 provides a signal to the motor control to cause the motor to run the lead screw by the requisite number of rotations.

The requisite number of lead screw rotations may be determined from the first and the second position signals in combination with the known pitch of the lead screw threads. Since the split nuts 66 are part of the screw drive mechanism 28 which is coupled to the driver position sensor 34, the first position signal is representative of the last known linear position, $X_E$, of the split nuts along the lead screw 26 in which the split nut threads were fully engaged with the lead screw threads. The second position signal is representative of the new linear position, $X_D$, of the split nuts along the lead screw. The pitch P, being the linear distance between the crests of the lead screw threads, corresponds to the linear distance associated with a single rotation of the lead screw. The function:

$$n'_R = \frac{\Delta X}{P} \quad (1)$$

where:
$n'_R$=the number of reverse rotations of the lead screw;
$\Delta X$=the difference between the positions $X_E$ and $X_D$;
P=the pitch of the lead screw threads;

gives the number of reverse rotations of the lead screw 26 required to move the split nuts 66 rearward from $X_E$ to $X_D$ had the split nuts 66 remained engaged with the lead screw 26. It is to be understood that the axial distance $\Delta X$ can be determined from a corresponding change in the position signal from the driver position sensor 34. Thus, the operator having disengaged the split nuts 66 and repositioned them to $X_D$, running the lead screw 26 by $n'_R$ reverse rotations will ensure full thread engagement.

Figure 11:
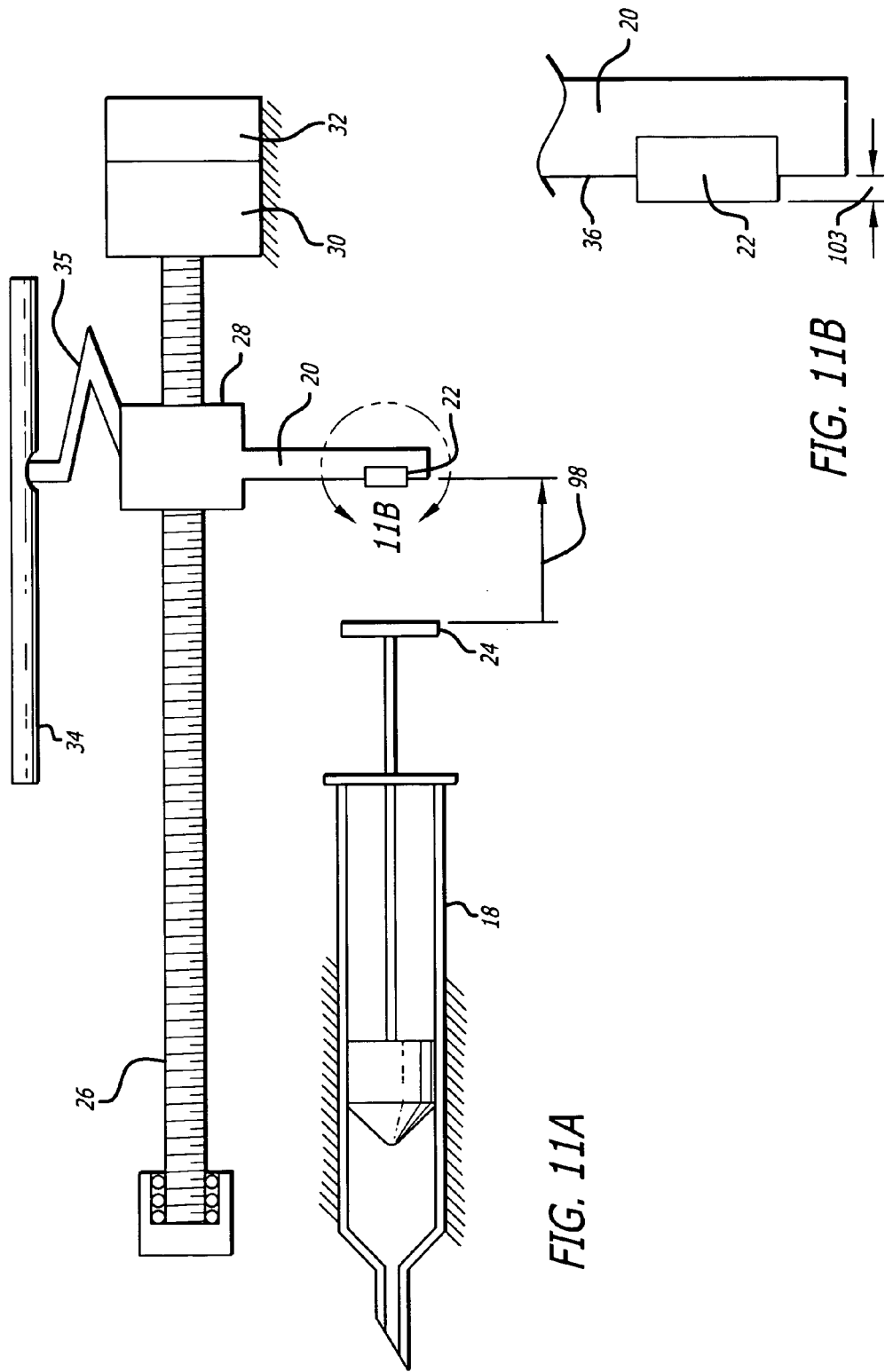
FIG. 11A presents a block diagram of a dynamic thread engagement system and shows a screw drive mechanism coupled to the plunger driver, the screw drive mechanism being retracted by the operator by a certain distance from the plunger of a syringe mounted in the syringe pump which is used by the processor to control thread alignment.
FIG. 11B presents a view of the distance the plunger sensor button of the plunger driver in FIG. 11A must travel from the point where the plunger sensor trips to the point where the button is flush with the front face of the plunger driver.
Figure 12:
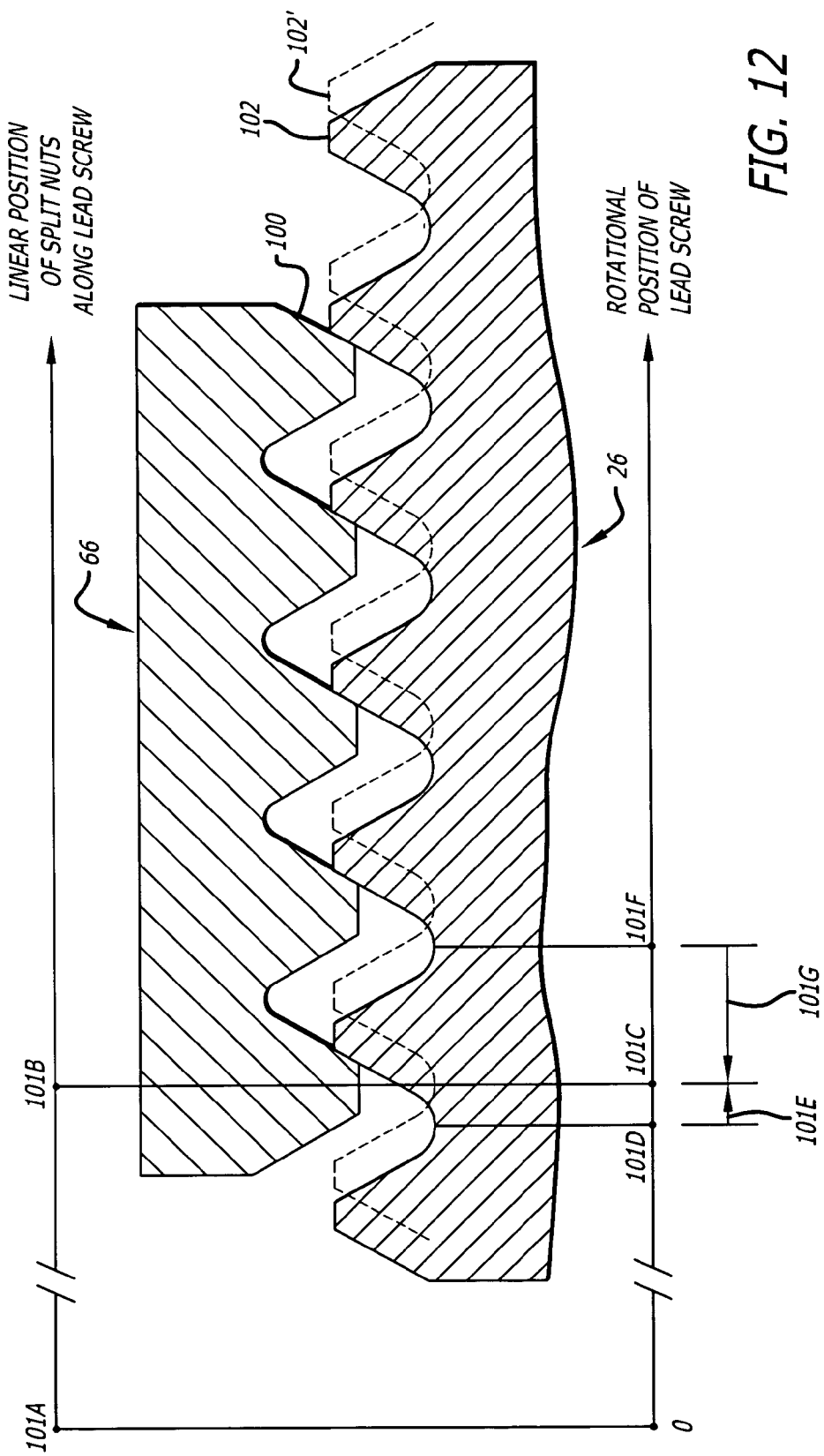
FIG. 12 presents a cross-sectional view of the threads of a lead screw that are misaligned with the threads of a split nut and shows in phantom lines the position that the lead screw threads must have for full thread engagement.

Referring now to FIG. 11A, FIG. 11B, and FIG. 12, there is shown a screw drive mechanism 28 wherein threads 100 of the splits nuts 66 have been disengaged by the operator from threads 102 of the lead screw 26 and then moved axially from $X_E$ to $X_D$ along the lead screw 26. Thus, the screw drive mechanism 28 and the split nuts 66 were moved an axial distance given by $\Delta X$, which is illustrated as arrow 98 in FIG. 11A. Referring to FIG. 12, the split nut threads 100 in position $X_E$ are shown with the lead screw threads 102 in a rotational position prior to running the lead screw 26 to ensure full thread engagement. Positions $X_E$ and XD are illustrated as points 101A and 101B. Lead screw threads 102' depicted in phantom lines indicate the desired rotational position of the lead screw threads 102 that will align the lead screw thread troughs with the split nut thread crests after $n'_R$ reverse rotations of the lead screw 26. In FIG. 12, $n'_R$ is illustrated as point 101C. It is to be understood that the number of reverse rotations can be reduced by any integer number, the maximum integer number being determined by truncating the value given by $n'_R$, as represented by TRUNC($n'_R$). Thus, the function:

$$n_R = n'_R - \text{TRUNC}(n'_R) \quad (2)$$

also gives the reverse rotations that will ensure full thread engagement. In FIG. 12, TRUNC ($n'_R$) is illustrated as point 101D, and $n_R$ is illustrated as arrow 101E which is the difference between points 101C and 101D. Reducing the number of rotations may be preferable to decrease the corresponding time to align the two sets of threads. It is to be further understood that the lead screw 26 can also be run in the forward direction and that the function:

$$n_F = \text{TRUNC}(n'_R + 0.99) - n'_R \quad (3)$$

gives the forward rotations that will ensure full thread engagement. In FIG. 12, TRUNC ($n'_R+0.99$) is illustrated as point 101F, and $n_F$ is illustrated as arrow 101G which is the difference between points 101F and 100C. Running in the forward direction may be preferable to simplify the system such that the motor need only be configured to run only in one direction. In addition, when $n_F$ is less than $n_R$, it will take less time to align the two sets of threads by running in the forward direction.

The above functions giving the number of forward and reverse rotations are exemplary in that other functions may be employed. For example, the number of rotations can be increased by any integer number of rotations. As further example, the number of forward rotations can also be determined from the number of reverse rotations subtracted from one full rotation, as given by the function:

$$n'_F = 1 - n_R \quad (4)$$

The function $n'_F$ differs from $n_F$ in that $n'_F$ gives a value of one, while $n_F$ gives zero, when $n_R$ and $n'_R$ are zero. The functions $n_R$ and $n_F$, which give the smallest amount of rotation in the reverse and forward directions, respectively, may be preferable as they correspond to shorter amounts of time to align the two sets of threads. Furthermore, it is to be understood that the first position signal can be representative of any sensed axial position of the split nuts 66 along the lead screw 26 in which the split nuts threads were fully engaged to the lead screw threads. It is contemplated that taking the first position signal immediately before the time of thread disengagement minimizes inaccuracies that may arise, such as due to a temperature differential over time.

By way of example only, in the event that the operator moves the plunger driver rearward by a distance of 5.359 cm (2.11 inches) on an infusion pump having a lead screw with a pitch of 0.127 cm (0.05 inches), a forward rotation of 288 degrees, being 0.80 of one full rotation, will ensure full thread engagement. A reverse rotation of 72 degrees, being 0.20 of one full rotation, will also ensure full thread engagement.

It is contemplated that inaccuracies in determining the requisite number of lead screw rotations could occur when taking the second position signal. As discussed above in association with FIG. 10, a change in the plunger signal prompts the processor to take the second position signal, which is assumed to represent the final position of the split nuts 66 along the lead screw 26. However, after the change in the plunger signal, the split nuts along with the plunger driver 20 may need to move a small but significant distance before the plunger driver presses against the syringe plunger. That distance, shown as reference numeral 103 in FIG. 11B, corresponds to the distance the plunger sensor button 22 travels, after the plunger sensor trips, to the point where the plunger sensor button is flush with the front plate 36 of the plunger driver such that the syringe plunger is in actual contact with the front plate. This distance depends on the position of the flag 48 relative to the plunger sensor 50 when the button is fully extended in front of the front plate. Thus, it is contemplated that the distance can be known in advance such that it can be used by the processor to more accurately determine the requisite number of lead screw rotations.

To increase accuracy, it is further contemplated that the driver position sensor can be used to detect syringe replacement and to infer that the split nuts threads are disengaged from the lead screw threads. This method, in contrast to using only the plunger sensor, may be preferable in the situation where the syringe pump is of a design that allows the operator to lift out the syringe without first pressing the activating lever and retracting the plunger driver rearward. Preferably, the processor receives and stores the first position signal near the time when the operator subsequently slides the plunger driver to accommodate another syringe, which might be hours later. Because retraction of the plunger driver is an indicator that the split nuts threads were disengaged by the operator, the first position signal is received and stored nearer the time of actual thread disengagement and, thus, minimizes inaccuracies that may arise, such as due to a temperature differential over time.

Figure 13:
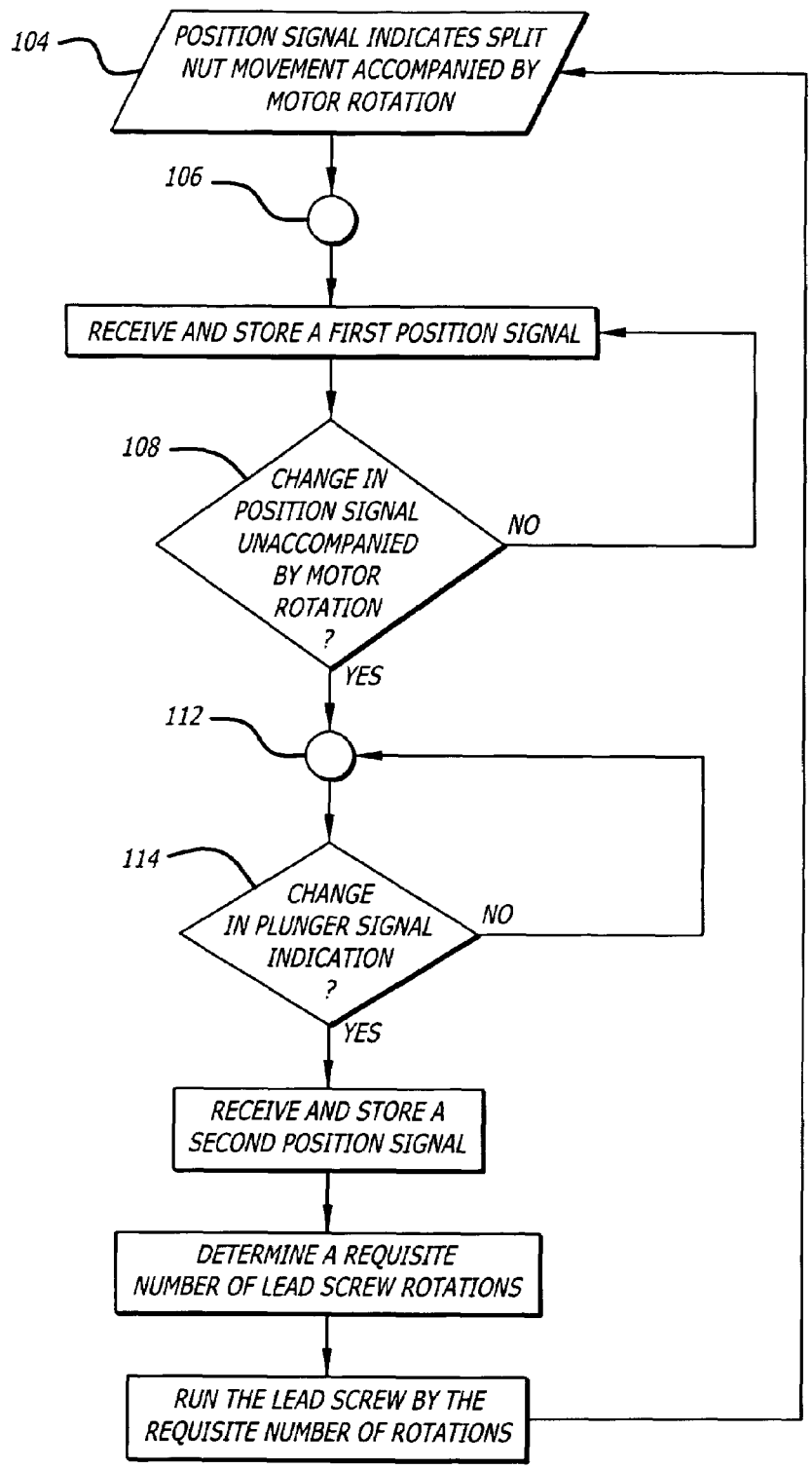
FIG. 13 presents a flow diagram of a dynamic engagement method using the signals from the plunger sensor and the driver position sensor to control thread alignment.

In FIG. 13 there is shown an operational flow diagram illustrating a method in which the position signal is used by the processor 86 to detect syringe replacement and to infer disengagement of the split nut threads from the lead screw threads. Between blocks 104 and 106 of the flow diagram, the operator lifts the first syringe out of the syringe pump. At some later time, between blocks 106 and 108, the operator presses the activating lever 74 to disengage the split nuts 66 and slides the plunger driver 20 rearward. Accordingly at block 108, the position signal from the driver position sensor 34 indicates movement of the split nuts along the lead screw 26. The processor infers from the change in the position signal unaccompanied by rotation of the motor that the split nuts threads have just disengaged from the lead screw threads. Before the change in the position signal, the processor 86 received and stored a first position signal from the driver position sensor. At block 112, subsequent to installing a second syringe in place of the first syringe, the operator slides the plunger driver forward so that it presses against the syringe plunger of the second syringe. Accordingly at block 114, the plunger signal now indicates that the plunger driver is engaged with the syringe plunger of the second syringe. Upon or after this indication, the processor receives and stores a second position signal from the driver position sensor. Using the first position signal and the second position signal, the processor determines a requisite amount of lead screw rotation ensuring that the split nut threads fully engage the lead screw threads. The requisite amount of rotation is determined as previously discussed in association with FIG. 9. The processor 86 then provides a signal to the motor control 32 to cause the motor 30 to rotate the lead screw by the requisite amount.

Figure 14:
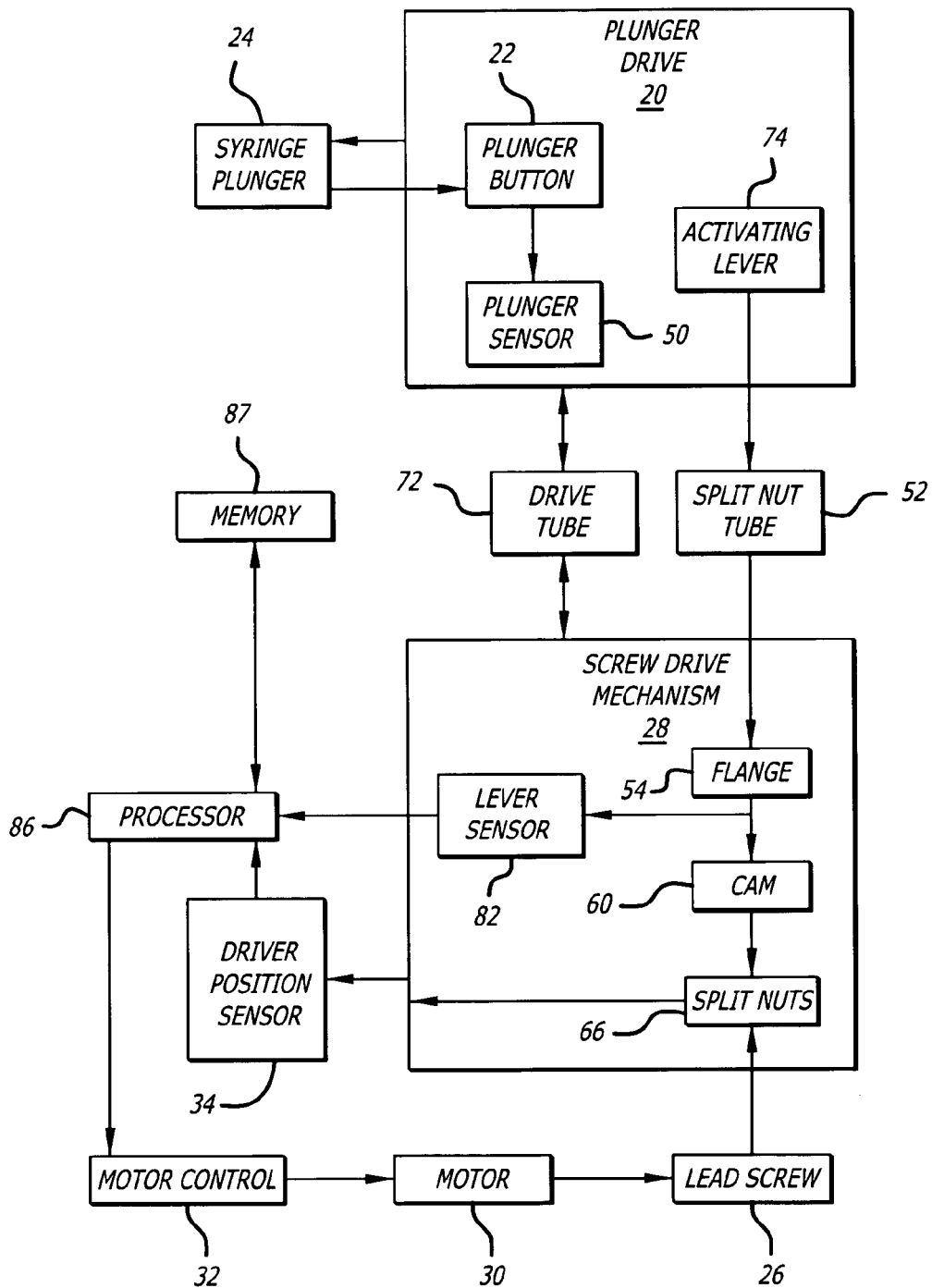
FIG. 14 presents a block diagram of a dynamic engagement system having signals from the lever sensor coupled to the processor to control thread alignment.
Figure 15:
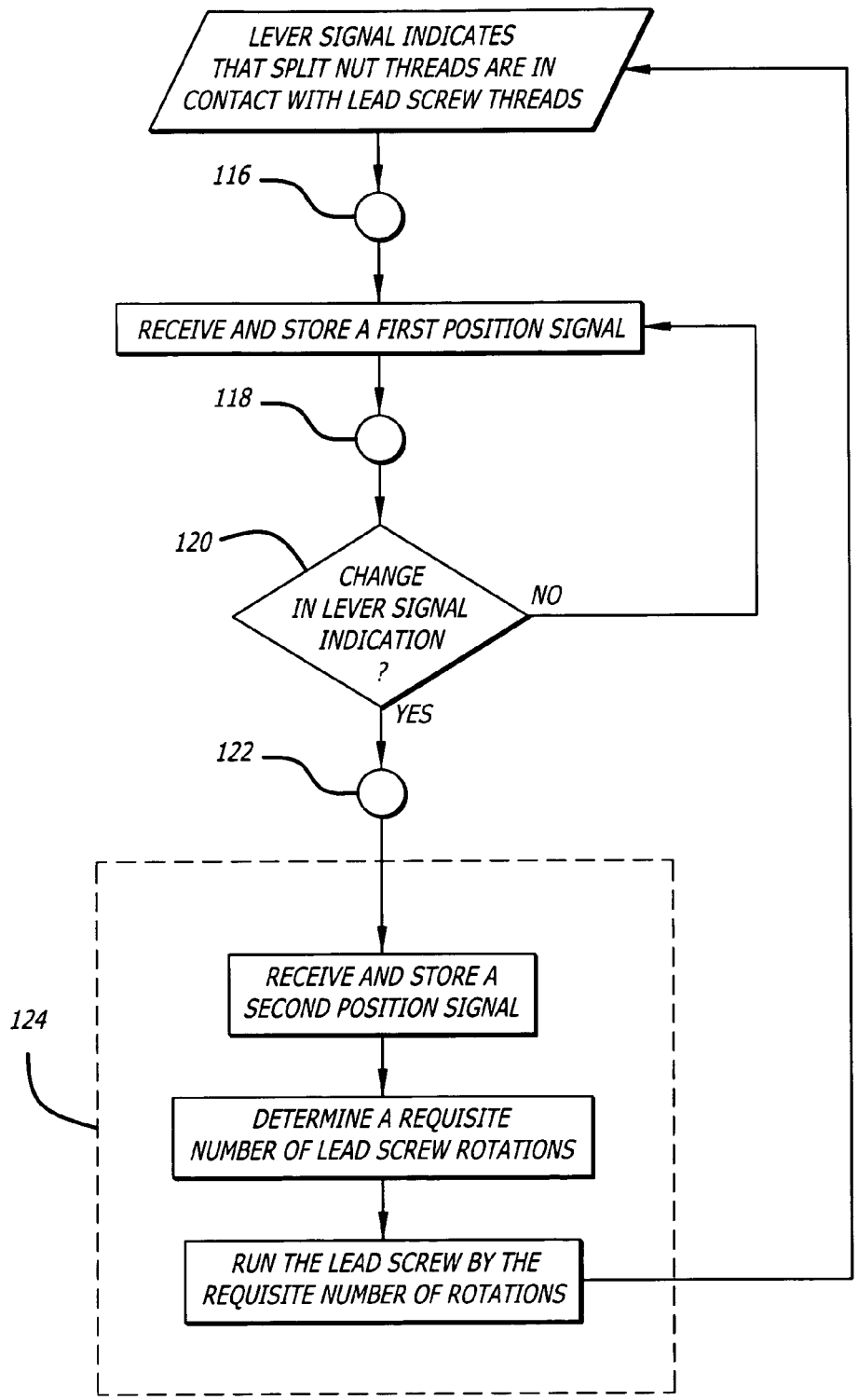
FIG. 15 presents a flow diagram of a dynamic engagement method using signals from the lever sensor to control thread alignment.

Accordingly, in FIG. 14 there is shown another embodiment having signals from the lever sensor 82 and the driver position sensor 34 coupled to the processor 86, and in FIG. 15 there is shown an operational flow diagram illustrating a method in which the lever signal is used by the processor to detect syringe replacement and infer the occurrence of disengagement of the split nut threads from the lead screw threads. At block 116 of the flow diagram, the operator lifts the first syringe out of the syringe pump. At some later time, at block 118, the operator begins to press the activating lever 74 to disengage the split nuts 66 from the lead screw 26. The operator then slides the plunger driver 20 rearward. Accordingly at block 120, the lever signal to the processor indicates that the split nuts are separated from the lead screw. Before this change in the lever signal, the processor received and stored the first position signal from the driver position sensor. At block 122, the operator begins to release the activating lever before installing the second syringe. As explained previously in association with FIG. 8, the lever signal changes indication with some time period remaining before the split nut threads make contact with the lead screw threads. During that remaining time period, illustrated as block 124, the processor receives and stores the second position signal from the driver position sensor. Using the thread pitch, the first position signal, and the second position signal, the processor determines the requisite amount of lead screw rotation ensuring that the split nut threads fully engage the lead screw threads, the requisite amount of rotation being determined as previously discussed in association with FIG. 9. The processor immediately provides a signal to the motor control 32 to cause the motor 30 to rotate the lead screw by the requisite amount before the split nut threads make contact with the lead screw threads. Upon such contact, the process begins again from the top of the flow diagram.

With continued reference to FIG. 15, at block 116 of the flow diagram, the operator installs the second syringe in the syringe pump 16. Then at block 118, the operator begins to press the activating lever 74 to disengage the split nuts 66 from the lead screw 26. The operator then slides the plunger driver 20 forward so that is presses against the syringe plunger. Accordingly at block 120, the lever signal to the processor 86 indicates that the split nuts are separated from the lead screw. Before this change in the lever signal, the processor received and stored the first position signal from the driver position sensor 34. At block 122, the operator begins to release the activating lever. During the remaining time period before the split nut threads make contact with the lead screw threads, the processor receives and stores the second position signal from the driver position sensor. Using the thread pitch, the first position signal, and the second position signal, the processor 86 determines the requisite amount of lead screw rotation ensuring that the split nut threads fully engage the lead screw threads, the requisite amount being determined as previously discussed in association with FIG. 9. The processor immediately provides a signal to the motor control 32 to cause the motor 30 to rotate the lead screw by the requisite amount before the split nut threads make contact with the lead screw threads.

In the case where the position sensor 34 is electrical in nature, it will provide different voltages (or currents, or other energy level) in accordance with the position of the screw drive mechanism along the position sensor. As it relates to the syringe pump being discussed herein, the finger-like wiper 35 (FIG. 5) presses on the position sensor. At the point pressed, the position sensor provides a unique voltage. For example, at one end of travel of the screw drive mechanism 28, the position sensor may provide a voltage $V_1$ and at the other end of travel of the screw drive mechanism, the position sensor may provide a second voltage $V_2$, different from $V_1$. At the factory, the voltage/distance conversion factor may be determined and programmed into the processor 86. Where the position sensor is linear and is equal in length to the portion of the length of the lead screw being used for travel by the screw drive mechanism, the position of the screw drive mechanism along the linear position sensor equals the position of the screw drive mechanism along the lead screw. Thus the exact position of the screw drive mechanism can be determined from the voltage provided by the position sensor. Combining this with the known pitch of the lead screw threads, which is also the pitch of the split nut threads, the position along the lead screw of the screw drive mechanism can be determined from the voltage output by the position sensor. The processor can determine the change $\Delta X$ in the axial position with a voltage-to-distance conversion factor G such as by the formula:

$$\Delta X = G \cdot \Delta V \qquad (5)$$

where:

$\Delta V$=the difference in volts between $V_2$ and $V_1$;

$\Delta X$=the change in the axial position of the screw drive mechanism along the lead screw mechanism in units of distance; and G=the conversion factor from volts to the units of distance.

Initially, the conversion factor G for the position sensor 34 is determined during the manufacturing process. Over time, the accuracy of the position sensor may shift such that the computed value for $\Delta X$ based on G does not correspond to the actual axial distance $\Delta X$ of the screw drive mechanism along the position sensor, and the lead screw. When this occurs, the processor will not rotate the lead screw the correct amount and the split nut threads will fail to fully engage the lead screw threads because an inaccurate value for $\Delta X$ was used to determine $n_R$ and $n_F$. Thus, it will be appreciated that corrections to the conversion factor G are desirable.

Figure 16:
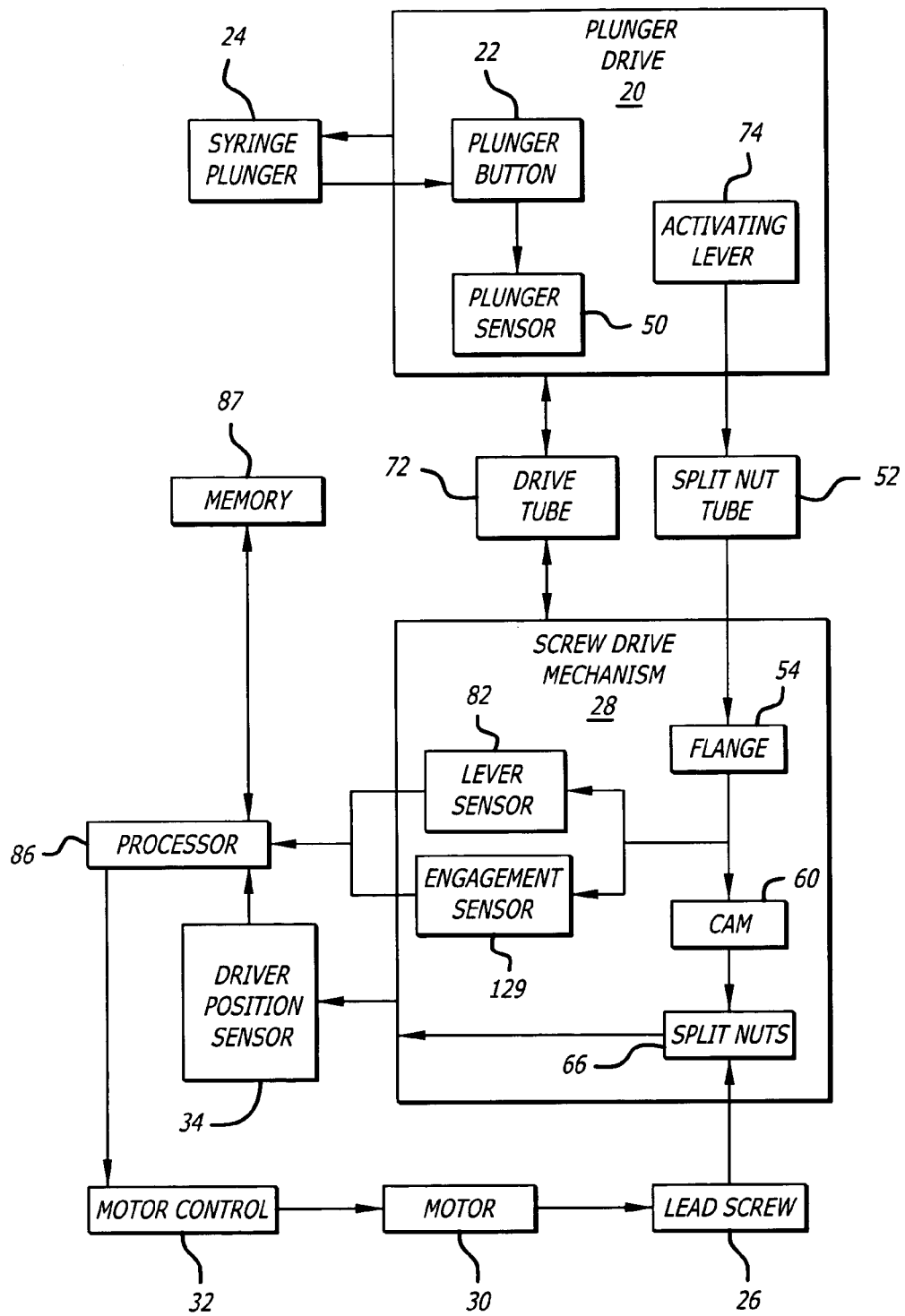
FIG. 16 presents a block diagram of a dynamic engagement system having signals from a lever sensor and an engagement sensor coupled to the processor.

In an embodiment of the present invention, an engagement sensor is employed to make corrections to the conversion factor G as described in detail below in connection with FIG. 17. The engagement sensor 129, shown schematically in FIG. 16, provides an engagement signal that is representative of the radial distance between the crests of the threads of the split nuts 66 and the troughs of the threads of the lead screw 26. The radial distance is not to be confused with the axial distance $\Delta X$. As used herein, the radial distance is perpendicular to the rotational axis running along the length of the lead screw 26. Thus, an indication that the radial distance is insignificant or non-existent is also an indication that the threads are fully engaged.

Referring back to FIG. 7, the engagement sensor 129 may comprise a third optical sensor mounted on the platform 84 forming part of the split nut housing 68. There is also shown a second flange 130 on the splut nut tube 52. Pressing the activating lever 74 to separate the split nuts 66 from the lead screw 26 rotates a flag 131 on the second flange 130. The trip point for the engagement sensor 129 depends on the position of the flag 131 relative to the sensor. Referring again to FIG. 8, the curvilinear relationship between rotation of the activating lever 74 and the radial distance between the threads is shown. Preferably, the trip point is set at a point 132 on the curve 75 corresponding to full engagement of the threads of the split nuts 66 with the threads of the lead screw 26. An engagement sensor signal is provided indicating full thread engagement when the radial distance falls below the trip point 132.

Figure 17:
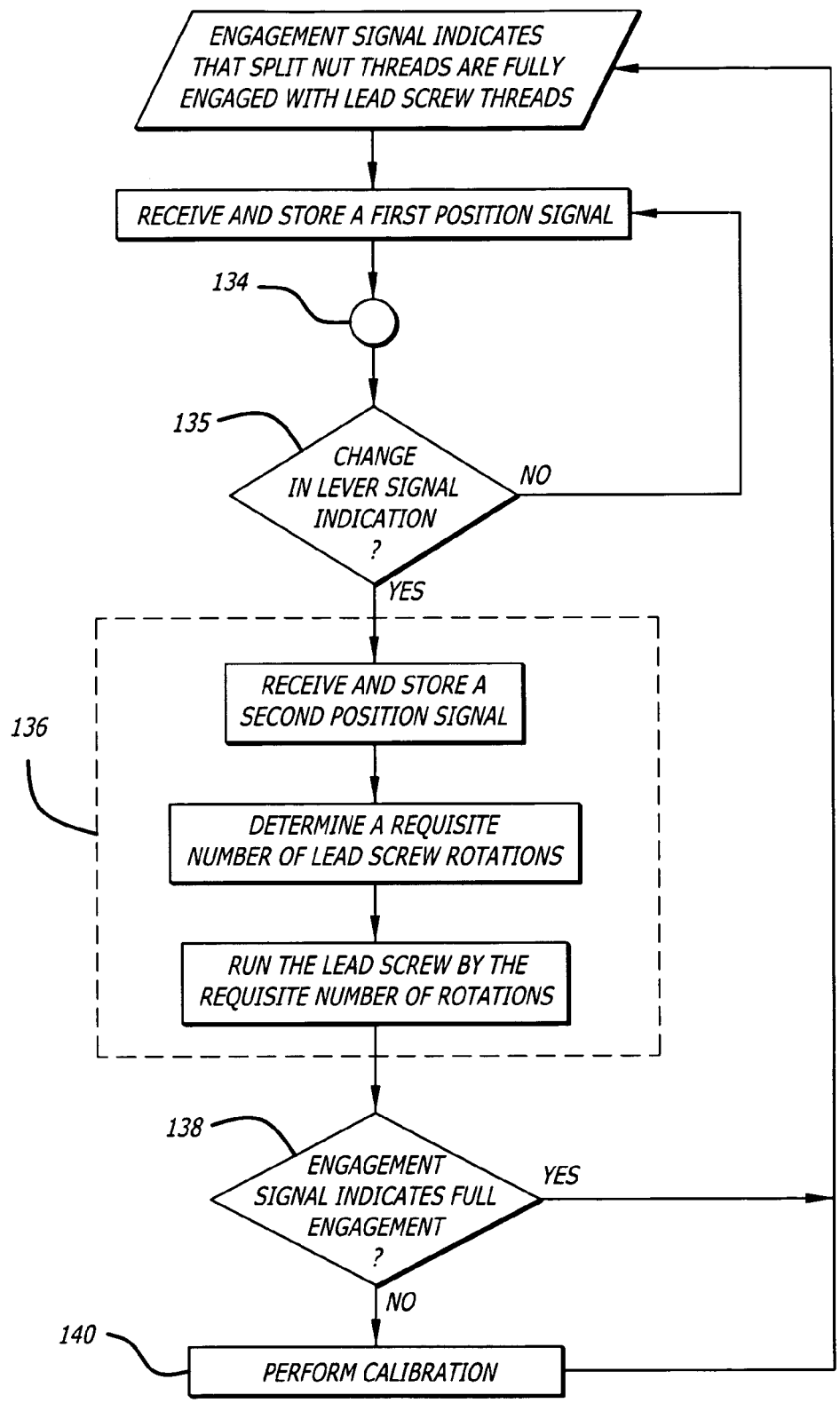
FIG. 17 presents a flow diagram of a dynamic engagement method using the engagement signals from the engagement sensor to indicate that the threads of the split nuts and the thread of the lead screw are fully engaged.

Referring now to FIG. 17, before the operator moves the plunger driver 38, the engagement signal indicates that the split nut threads are fully engaged with the lead screw threads. At block 134 of the flow diagram, the operator begins to press the activating lever 74 to separate the split nuts 66 from the lead screw 26. Accordingly, at block 135, the lever signal indicates that the activating lever 74 has been pressed. Before this change in the lever signal, the processor 86 received and stored the first position signal $V_1$ from the driver position sensor 34. Between blocks 135 and 136, the operator brings the plunger driver 20 to a new position $X_D$ and begins to release the activating lever such that the lever signal changes. At block 136, during a remaining time period before the split nut threads make contact with the lead screw threads, the processor receives and stores the second position signal $V_2$ from the driver position sensor. Using G, the processor determines the requisite amount of lead screw rotation intended to ensure that the split nut threads fully engage the lead screw threads. The processor immediately provides a signal to the motor control 32 to cause the motor 30 to rotate the lead screw by the requisite amount before the split nut threads make contact with the lead screw threads. At block 138, after the threads make contact, the engagement signal provides an indication of the radial distance at which the split nuts threads have dropped toward the lead screw threads. When the split nut threads have dropped sufficiently into the lead screw threads such that the threads are fully engaged, no further rotation of the lead screw or correction to the conversion factor G is required. Otherwise, a calibration procedure is automatically performed at block 140.

Preferably, the calibration procedure is performed whenever the activating lever 74 has been released by the operator and the split nut threads fail to fully engage the lead screw threads. The procedure includes rotating the lead screw a second time until the split nut threads fully engage the lead screw threads, followed by making a correction to the conversion factor G in this embodiment. Initially, the lead screw is preferably rotated by a small amount in one direction, such as for example 0.10 of one full rotation. Rotation is continued in the that direction until the engagement signal indicates full thread engagement, wherein the crests of the split nuts threads have dropped sufficiently into the troughs of the lead screw threads and vice versa. If the engagement signal fails to indicate full thread engagement after 0.10 of one full rotation, the lead screw is rotated in the opposite direction until the engagement signal indicates full thread engagement. At such time that the engagement signal indicates full thread engagement, the lead screw 26 will have rotated by a known amount $n_E$, which represents the change in the rotational position of the lead screw after block 136 of FIG. 17. Based on $n_E$ and the present value of G (referred to as $G_0$), the processor 86 determines and stores a corrected value of G, according to the following formula:

$$G = \frac{n_E P + (G_O \cdot \Delta V)}{\Delta V} \quad (6)$$

where:
G=the corrected conversion factor from volts to the units of distance;

$n_E$=the amount of rotation during the calibration procedure;
P=the thread pitch of the lead screw;
$G_0$=the present value of the conversion factor from volts to the units of distance; and
$\Delta V$=the difference in volts between $V_2$ and $V_1$.

It will be appreciated that the corrected value of G may be determined using other formulas based on $n_E$. For example, when the lead screw is rotated by an amount $n_E$ in the reverse direction, a corrected value of G may be determined by the formula:

$$G = G_0 \left( \frac{n_E + n'_R}{n'_R} \right) \quad (7)$$

where:
G=the corrected conversion factor from volts to the units of distance;
$G_0$=the present value of the conversion factor from volts to the units of distance;
$n_E$=the amount of rotation during the calibration procedure; and
$n'_R$=the number of reverse rotations of the lead screw.

The next time the operator moves the plunger driver 38 (between blocks 135 and 136 of FIG. 17), the corrected value of G will be used by the processor to determine the requisite amount of lead screw rotation (block 136 of FIG. 17).

By way of example only, an infusion pump may have a lead screw with a thread pitch of 0.127 cm (0.05 in) and a position sensor that develops a 4 volt increase in its position signal when its wiper that is connected to the screw drive mechanism 28 is moved rearward by an axial distance of 2.540 cm (1.000 in). As such, the position sensor has a conversion factor G of 0.2500 in/v. When the operator moves the plunger driver rearward by an axial distance $\Delta X$ causing the position signal to increase by 8.440 v, the processor will determine the axial distance $\Delta X$ to be 5.359 cm (2.110 in) and will rotate the lead screw in the reverse direction by an amount $n_R$ equivalent to 0.20 of one full rotation. However, the actual axial distance moved $\Delta X$ may not be 5.359 cm (2.110 in). In such an event, the lead screw may need to be run in the reverse direction by an additional amount $n_E$ equivalent to 0.10 of one full rotation before the threads of the split nuts and the lead screw fully engage. Accordingly, the processor will change the conversion factor G from, in this embodiment, 0.2500 in/v to 0.2506 in/v. If the operator again moves the plunger rearward causing the position signal to increase by 8.440 volts, the processor will determine the axial distance $\Delta X$ to be 5.372 cm (2.115 in) in the rearward direction and will rotate the lead screw in the reverse direction by an amount $n_R$ equivalent to 0.30 of one full rotation.

From the foregoing, it will be appreciated that the dynamic lead screw engagement system and method in accordance with the principles of the invention reduces the occurrence of delayed and excessive fluid infusion associated with misalignment of the split nut threads and lead screw threads in an infusion pump. Further, the use of the driver position sensor in accordance with the invention results in more accurate alignment of the split nut threads and lead screw threads. A dynamic lead screw engagement system and method in accordance with the aspects of the invention results in more accurate delivery of medicines to the patient and is particularly useful when low flow rates are required for the patient.

While several particular forms of the invention have been illustrated and described, it will also be apparent that various modifications can be made without departing from the scope of the invention. For example, the signals from the plunger sensor and lever sensor may be used in any variety of suitable ways in conjunction with the signal from the driver position sensor. As further example, any variety of suitable plunger sensors, lever sensors or driver position sensors may be used. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

I claim:

1. A system for aligning threads of a lead screw with threads of a screw drive mechanism, the screw drive mechanism operating to translate rotational motion of the lead screw into linear motion when their threads are fully engaged with each other, the system comprising:
    a motor coupled to the lead screw that selectively rotates the lead screw;
    a plunger driver coupled to the screw drive mechanism to selectively engage a syringe plunger for movement of the plunger in response to movement of the screw drive mechanism;
    a position sensor that provides a position signal representative of an axial position of the screw drive mechanism along the lead screw;
    a release device that disengages the threads of the screw drive mechanism from engagement with the threads of the lead screw thereby allowing an operator to move the screw drive mechanism to a selected position along the lead screw at which the threads of the screw drive mechanism may be re-engaged with the threads of the lead screw; and
    a processor that receives position signals from the position sensor and controls the motor to rotate the lead screw to a predetermined rotational position based on the position signals;
    wherein, the processor receives a position signal from the position sensor indicative of the position at which an operator is re-engaging the threads of the screw drive mechanism with the threads of the lead screw; and
    the processor controls the motor to rotate the lead screw to a rotational position at which the threads of the lead screw are aligned with the threads of the screw drive mechanism at the selected position.

2. The system for aligning threads of claim 1 wherein:
    the threads of the lead screw have a pitch;
    the threads of the screw drive mechanism have a pitch;
    the processor controls the motor to rotate the lead screw to a rotational position at which the threads of the lead screw are aligned with the threads of the screw drive mechanism as the lead screw and screw drive mechanism threads are being re-engaged, based on receipt of the position signal and based on the thread pitch of at least one of the lead screw and the screw drive mechanism.

3. The system for aligning threads of claim 1 comprising a memory in which is stored a reference position along the lead screw at which the threads of the screw drive mechanism and the threads of the lead screw have been aligned and fully engaged with each other;
    wherein the processor receives the position signal, compares the position signal to the reference position, and, based on the reference position and the position signal, controls the motor to rotate the lead screw to the rotational position at which the threads of the lead screw are aligned with the threads of the screw drive mechanism as the lead screw and screw drive mechanism threads are being re-engaged.

4. The system for aligning threads of claim 3 further comprising a syringe plunger sensor that provides a plunger sensor signal upon detecting the engagement of a syringe plunger with the plunger driver;
    wherein upon the processor receiving the plunger sensor signal, the processor compares the position signal to the reference position, and controls the motor to rotate the lead screw to the rotational position at which the threads of the lead screw are aligned with the threads of the screw drive mechanism as the lead screw and screw drive mechanism threads are being re-engaged based on the reference position and the position signal.

5. The system for aligning threads of claim 4 wherein upon the processor receiving the plunger sensor signal, receives the position signal, the processor compares the position signal to the reference position, and controls the motor to rotate the lead screw to the rotational position at which the threads of the lead screw are aligned with the threads of the screw drive mechanism as the lead screw and screw drive mechanism threads are being re-engaged based on the reference position and the position signal.

6. The system for aligning threads of claim 1 further comprising a thread engagement sensor that provides a thread engagement signal upon detecting that the threads of the screw drive mechanism are fully engaged with the threads of the lead screw;
    wherein upon receiving the thread engagement signal, the processor stores the position of the screw drive mechanism along the lead screw as a reference position; and
    wherein the processor receives the position signal, compares the position signal to the reference position, and controls the motor to rotate the lead screw to the rotational position at which the threads of the lead screw are aligned with the threads of the screw drive mechanism as the lead screw and screw drive mechanism threads are being re-engaged based on the reference position and the position signal.

7. The system for aligning threads of claim 6 further comprising a syringe plunger sensor that provides a plunger sensor signal upon detecting the engagement of a syringe plunger with the plunger driver;
    wherein upon the processor receiving the plunger sensor signal, the processor compares the position signal to the reference position and controls the motor to rotate the lead screw to the rotational position at which the threads of the lead screw are aligned with the threads of the screw drive mechanism as the lead screw and screw drive mechanism threads are being re-engaged based on the reference position and the position signal.

8. The system for aligning threads of claim 7 wherein upon the processor receiving the plunger sensor signal the processor receives the position signal, compares the position signal to the reference position, and controls the motor to rotate the lead screw to the rotational position at which the threads of the lead screw are aligned with the threads of the screw drive mechanism as the lead screw and screw drive mechanism threads are being re-engaged based on the reference position and the position signal.

9. The system for aligning threads of claim 1 wherein:
    the position sensor provides an electrical position signal representative of the axial position of the screw drive mechanism in relation to the lead screw;

the processor receives the position signal and processes it with a conversion factor to determine the axial location of the screw drive mechanism in relation to the lead screw.

10. The system for aligning threads of claim 9 further comprising a thread engagement sensor that provides a thread engagement signal upon detecting that the threads of the screw drive mechanism are fully engaged with the threads of the lead screw;
    wherein upon receiving the thread engagement signal, the processor stores the position of the screw drive mechanism along the lead screw as a reference position; and
    wherein the processor receives the position signal, compares the position signal to the reference position, and controls the motor to rotate the lead screw to the rotational position at which the threads of the lead screw are aligned with the threads of the screw drive mechanism as the lead screw and screw drive mechanism threads are being re-engaged based on the reference position and the position signal.

11. The system for aligning threads of claim 10 wherein the processor monitors the thread engagement signal upon re-engagement of the threads of the screw drive mechanism with the threads of the led screw and if the thread engagement signal is not received, the processor alters the conversion factor.

12. A method for aligning threads of a lead screw with threads of a screw drive mechanism, the screw drive mechanism operating to translate rotational motion of the lead screw into linear motion when their threads are fully engaged with each other, the method comprising:
    selectively rotating the lead screw;
    selectively engaging a syringe plunger with a plunger driver coupled to the screw drive mechanism for movement of the syringe plunger in response to movement of the screw drive mechanism;
    sensing an axial position of the screw drive mechanism along the lead screw with a position sensor that provides a position signal representative thereof;
    disengaging the threads of the screw drive mechanism from engagement with the threads of the lead screw with a release device that thereby allows an operator to move the screw drive mechanism to a selected position along the lead screw at which the threads of the screw drive mechanism may be re-engaged with the threads of the lead screw; and
    controlling the motor to rotate the lead screw to a predetermined rotational position based on the position signal;
    wherein the position signal is indicative of the position at which an operator is re-engaging the threads of the screw drive mechanism with the threads of the lead screw; and
    controlling the motor includes rotating the lead screw to a rotational position at which the threads of the lead screw are aligned with the threads of the screw drive mechanism at the selected position.

* * * * *